United States Patent
Gadbois

(10) Patent No.: US 10,507,080 B2
(45) Date of Patent: Dec. 17, 2019

(54) ORTHODONTIC ANCHOR SYSTEM

(71) Applicant: Anthony M Gadbois, Columbia, MO (US)

(72) Inventor: Anthony M Gadbois, Columbia, MO (US)

( * ) Notice: Subject to any disclaimer, the term of this patent is extended or adjusted under 35 U.S.C. 154(b) by 0 days.

(21) Appl. No.: 15/610,659

(22) Filed: Jun. 1, 2017

(65) Prior Publication Data
US 2017/0354481 A1     Dec. 14, 2017

Related U.S. Application Data

(60) Provisional application No. 62/348,161, filed on Jun. 10, 2016.

(51) Int. Cl.
*A61C 7/08* (2006.01)
*A61C 7/30* (2006.01)

(52) U.S. Cl.
CPC ............... *A61C 7/08* (2013.01); *A61C 7/303* (2013.01)

(58) Field of Classification Search
CPC .... A61C 7/08; A61C 7/10; A61C 7/36; A61C 7/06; A61C 7/303
See application file for complete search history.

(56) References Cited

U.S. PATENT DOCUMENTS

| | | | | |
|---|---|---|---|---|
| 3,724,075 A * | 4/1973 | Kesling | ............... | A61C 7/08 433/6 |
| 4,609,349 A * | 9/1986 | Cain | ............... | A61C 7/00 433/18 |
| 5,645,423 A * | 7/1997 | Collins, Jr. | ............... | A61C 7/36 433/18 |
| 6,450,167 B1 * | 9/2002 | David | ............... | A61C 7/08 128/848 |
| 7,837,468 B2 * | 11/2010 | Teng | ............... | A61C 17/20 433/21 |
| 2010/0075269 A1 * | 3/2010 | Mutschler | ............... | A61C 7/00 433/10 |
| 2013/0089828 A1 * | 4/2013 | Borovinskih | ............... | A61C 7/08 433/6 |
| 2013/0230819 A1 * | 9/2013 | Arruda | ............... | A61C 7/22 433/6 |
| 2013/0323664 A1 * | 12/2013 | Parker | ............... | A61C 7/10 433/6 |

OTHER PUBLICATIONS

ASM Aerospace Specification Metals, Inc. "AISI Type 316 Stainless Steel". Dec. 31, 2011. Accessed at http://asm.matweb.com/search/SpecificMaterial.asp?bassnum=mq316j on Mar. 26, 2019 (Year: 2011).*

Gordon England "Calculator for Conversion between Vickers Hardness Number and SI Units MPa and GPa". Accessed at http://www.gordonengland.co.uk/hardness/hvconv.htm (Year: 2019).*

* cited by examiner

*Primary Examiner* — Edward Moran
(74) *Attorney, Agent, or Firm* — SBMC

(57) ABSTRACT

An orthodontic anchor system may include an anchor system having an anchor system distal end and an anchor system proximal end. The anchor system may include an aligner receptacle, an aligner housing, an anchor mechanism, and an elastic band receptacle. The aligner housing may be configured to house an aligner. The anchor mechanism may be configured to house an elastic band. The aligner housing may be configured to house the aligner without requiring a modification of the aligner.

20 Claims, 13 Drawing Sheets

ORTHODONTIC ANCHOR SYSTEM

CROSS-REFERENCE TO RELATED APPLICATIONS

This Application claims the benefit of U.S. Provisional Application No. 62/348,161, filed Jun. 10, 2016.

FIELD OF THE INVENTION

The present disclosure relates to an orthodontic system, and, more particularly, to an orthodontic anchor system.

BACKGROUND OF THE INVENTION

Clear-aligner treatment uses a plurality of customized aligners to adjust a patient's teeth. Each aligner applies pressure to a patient's tooth or teeth which causes the tooth or teeth to move into a particular position within the aligner. If a patient's teeth require rotation or extrusion, then aligners alone may be insufficient to achieve such movement. In order to achieve rotation or extrusion of a particular tooth an elastic band may be used to apply a force to the particular tooth. This is typically accomplished by bonding a button to the particular tooth to establish a first anchor point and then disposing an elastic band over the button and a second anchor point. The elastic band applies a force to the button and the particular tooth causing the tooth to gradually move towards the second anchor point. A practitioner selects a second anchor point to apply a specific force vector to a button and a particular tooth wherein the specific force vector has a direction configured to move the particular tooth into a particular position within an aligner. A practitioner is generally limited in selection of a second anchor point by considerations of patient comfort and availability of potential anchor sites.

BRIEF SUMMARY OF THE INVENTION

An orthodontic anchor system is presented. In one or more embodiments, an orthodontic anchor system may comprise an anchor system having an anchor system distal end and an anchor system proximal end. Illustratively, the anchor system may comprise an aligner receptacle, an aligner housing, an anchor mechanism, and an elastic band receptacle. In one or more embodiments, the aligner housing may be configured to house an aligner. Illustratively, the anchor mechanism may be configured to house an elastic band. In one or more embodiments, the aligner housing may be configured to house the aligner without requiring a modification of the aligner.

BRIEF DESCRIPTION OF THE DRAWINGS

The above and further advantages of the present invention may be better understood by referring to the following description in conjunction with the accompanying drawings in which like reference numerals indicate identical or functionally similar elements.

DETAILED DESCRIPTION OF AN ILLUSTRATIVE EMBODIMENT

Figure 1:
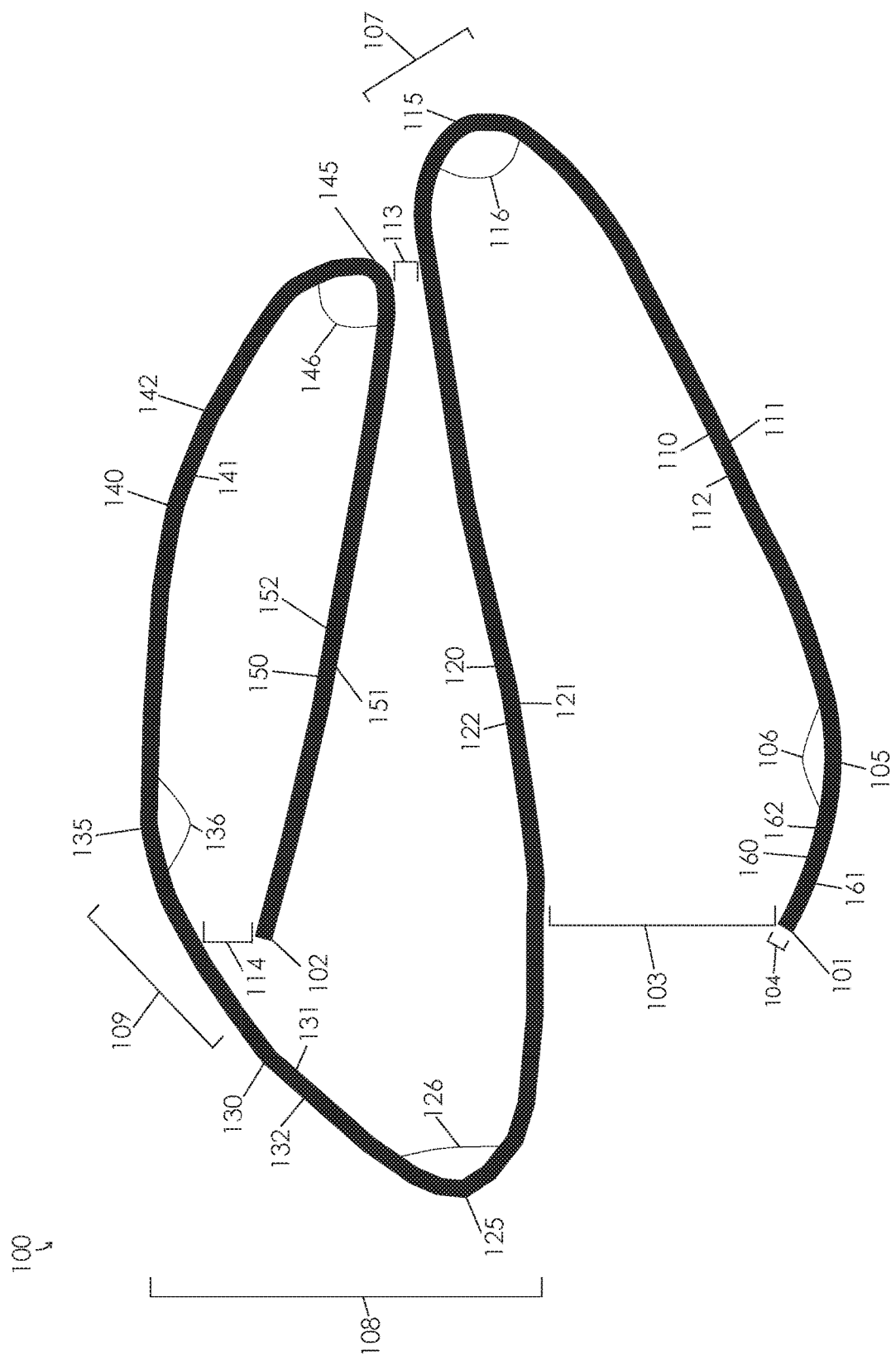
FIG. 1 is a schematic diagram illustrating an anchor system.

FIG. 1 is a schematic diagram illustrating an anchor system 100. In one or more embodiments, an anchor system 100 may comprise an anchor system distal end 101 and an anchor system proximal end 102. Illustratively, anchor system 100 may comprise an aligner receptacle 103 and an anchor mechanism 108. In one or more embodiments, aligner receptacle 103 may comprise an aligner housing 107, an aligner inferior interface limb 110, and an aligner superior interface limb 120. Illustratively, aligner superior interface limb 120 may comprise an aligner superior interface limb inferior surface 121 and an aligner superior interface limb superior surface 122. In one or more embodiments, aligner inferior interface limb 110 may comprise an aligner inferior interface limb inferior surface 111 and an aligner inferior interface limb superior surface 112. Illustratively, aligner housing 107 may be disposed between aligner inferior interface limb 110 and aligner superior interface limb 120, e.g., aligner housing 107 may be disposed between aligner inferior interface limb superior surface 112 and aligner superior interface limb inferior surface 121.

Illustratively, anchor system 100 may comprise a spring mechanism 160 having a spring mechanism inferior surface 161 and a spring mechanism superior surface 162. In one or more embodiments, spring mechanism 160 may have a spring mechanism thickness 104 configured to minimize patient discomfort. Illustratively, spring mechanism thickness 104 may comprise a length between spring mechanism inferior surface 161 and spring mechanism superior surface 162. In one or more embodiments, spring mechanism thickness 104 may be length in a range of 0.01 to 0.30 millimeters, e.g., spring mechanism thickness 104 may be a length of 0.10 millimeters. Illustratively, spring mechanism thickness 104 may be a length of less than 0.01 millimeters or greater than 0.30 millimeters.

In one or more embodiments, anchor system 100 may comprise a first joint 105 and a first joint angle 106. Illustratively, spring mechanism 160 may be disposed between anchor system distal end 101 and first joint 105. In one or more embodiments, first joint 105 may be configured to connect spring mechanism 160 and aligner inferior interface limb 110, e.g., first joint 105 may be disposed between spring mechanism 160 and aligner inferior interface limb 110. Illustratively, first joint angle 106 may comprise any angle greater than or equal to 90.0 degrees, e.g., first joint angle 106 may comprise an angle in a range of 90.0 to 180.0 degrees. In one or more embodiments, first joint angle 106 may comprise an angle in a range of 120.0 to 175.0 degrees, e.g., first joint angle 106 may comprise an angle of 165.0 degrees. Illustratively, first joint angle 106 may comprise an angle less than 120.0 degrees or greater than 175.0 degrees.

In one or more embodiments, anchor system 100 may comprise a second joint 115 and a second joint angle 116. Illustratively, aligner inferior interface limb 110 may be disposed between first joint 105 and second joint 115. In one or more embodiments, second joint 115 may be configured to connect aligner inferior interface limb 110 and aligner superior interface limb 120, e.g., second joint 115 may be disposed between aligner inferior interface limb 110 and aligner superior interface limb 120. Illustratively, second joint angle 116 may comprise any angle less than or equal to 90.0 degrees, e.g., second is joint angle 116 may comprise an angle in a range of 10.0 to 90.0 degrees. In one or more embodiments, second joint angle 116 may comprise an angle in a range of 20.0 to 80.0 degrees, e.g., second joint angle 116 may comprise an angle of 65.0 degrees. Illustratively, second joint angle 116 may comprise an angle less than 20.0 degrees or greater than 80.0 degrees.

In one or more embodiments, anchor mechanism 108 may comprise an elastic band receptacle 109, an anchor mechanism anterior limb 130, an anchor mechanism posterior limb 140, and an elastic band retaining limb 150. Illustratively, anchor mechanism anterior limb 130 may comprise an anchor mechanism anterior limb inferior surface 131 and an anchor mechanism anterior limb superior surface 132. In one or more embodiments, anchor system 100 may comprise a third joint 125 and a third joint angle 126. Illustratively, third joint 125 may be configured to connect anchor mechanism anterior limb 130 and aligner superior interface limb 120, e.g., third joint 125 may be disposed between anchor mechanism anterior limb 130 and aligner superior interface limb 120. In one or more embodiments, third joint angle 126 may comprise any angle less than or equal to 100.0 degrees, e.g., third joint angle 126 may comprise an angle in a range of 20.0 to 100.0 degrees. Illustratively, third joint angle 126 may comprise an angle in a range of 30.0 to 90.0 degrees, e.g., third joint angle 126 may comprise an angle of 75.0 degrees. In one or more embodiments, third joint angle 126 may comprise an angle less than 30.0 degrees or greater than 90.0 degrees.

Illustratively, anchor mechanism posterior limb 140 may comprise an anchor mechanism posterior limb inferior surface 141 and an anchor mechanism posterior limb superior surface 142. In one or more embodiments, anchor system 100 may comprise a fourth joint 135 and a fourth joint angle 136. Illustratively, fourth joint 135 may be configured to connect anchor mechanism posterior limb 140 and anchor mechanism anterior limb 130, e.g., fourth joint 135 may be disposed between anchor mechanism posterior limb 140 and anchor mechanism anterior limb 130. In one or more embodiments, fourth joint angle 136 may comprise any angle greater than or equal to 90.0 degrees, e.g., fourth joint angle 136 may comprise an angle in a range of 90.0 to 180.0 degrees. Illustratively, fourth joint angle 136 may comprise an angle in a range of 110.0 to 175.0 degrees, e.g., fourth joint angle 136 may comprise an angle of 170.0 degrees. In one or more embodiments, fourth joint angle 136 may comprise an angle of less than 110.0 degrees or greater than 175.0 degrees.

Illustratively, elastic band retaining limb 150 may comprise an elastic band retaining limb inferior surface 151 and an elastic band retaining limb superior surface 152. In one or more embodiments, anchor system 100 may comprise a fifth joint 145 and a fifth joint angle 156. Illustratively, fifth joint 145 may be configured to connect elastic band retaining limb 150 and anchor mechanism posterior limb 140, e.g., fifth joint 145 may be disposed between elastic band retaining limb 150 and anchor mechanism posterior limb 140. In one or more embodiments, fifth joint angle 146 may comprise any angle less than or equal to 90.0 degrees, e.g., fifth joint angle 146 may comprise an angle in a range of 15.0 to 65.0 degrees. Illustratively, fifth joint angle 146 may comprise an angle in a range of 11.0 to 71.0 degrees, e.g., fifth joint angle 146 may comprise an angle of 53.0 degrees. In one or more embodiments, fifth joint angle 146 may comprise an angle of less than 11.0 degrees or greater than 71.0 degrees.

Illustratively, elastic band retaining limb 150 may be disposed between anchor system proximal end 102 and fifth joint 145. In one or more embodiments, elastic band retaining limb 150 may be disposed between anchor mechanism posterior limb 140 and aligner superior interface limb 120, e.g., elastic band retaining limb 150 may be disposed between anchor mechanism posterior limb inferior surface 141 and aligner superior interface limb superior surface 122. Illustratively, elastic band retaining limb 150 may be disposed between anchor mechanism anterior limb 130 and aligner superior interface limb 120, e.g., elastic band retaining limb 150 may be disposed between anchor mechanism anterior limb inferior surface 131 and aligner superior interface limb superior surface 122. In one or more embodiments, elastic band retaining limb 150 may be disposed between anchor mechanism posterior limb 140 and aligner inferior interface limb 110, e.g., elastic band retaining limb 150 may be disposed between anchor mechanism posterior limb inferior surface 141 and aligner inferior interface limb superior surface 112. Illustratively, elastic band retaining limb 150 may be disposed between anchor mechanism anterior limb 130 and aligner inferior interface limb 110, e.g., elastic band retaining limb 150 may be disposed between anchor mechanism anterior limb inferior surface 131 and aligner inferior interface limb superior surface 112.

In one or more embodiments, aligner superior interface limb 120 may be disposed between third joint 125 and second joint 115, e.g., third joint 125 may be configured to connect aligner superior interface limb 120 to anchor mechanism anterior limb 130 and second joint 115 may be configured to connect aligner superior interface limb 120 to aligner inferior interface limb 110. Illustratively, aligner superior interface limb 120 may be disposed between elastic band retaining limb 150 and aligner inferior interface limb 110, e.g., aligner superior interface limb 120 may be disposed between elastic band retaining limb inferior surface 151 and aligner inferior interface limb superior surface 112. In one or more embodiments, aligner superior interface limb 120 may be disposed between anchor mechanism posterior limb 140 and aligner inferior interface limb 110, e.g., aligner superior interface limb 120 may be disposed between anchor mechanism posterior limb inferior surface 141 and aligner inferior interface limb superior surface 112. Illustratively, aligner superior interface limb 120 may be disposed between anchor mechanism anterior limb 130 and aligner inferior interface limb 110, e.g., aligner superior interface limb 120 may be disposed between anchor mechanism anterior limb inferior surface 131 and aligner inferior interface limb superior surface 112. In one or more embodiments, aligner superior interface limb 120 may be disposed between elastic band retaining limb 150 and spring mechanism 160, e.g., aligner superior interface limb 120 may be disposed between elastic band retaining limb inferior surface 151 and spring mechanism superior surface 162. Illustratively, aligner superior interface limb 120 may be disposed between anchor mechanism posterior limb 140 and spring mechanism 160, e.g., aligner superior interface limb 120 may be disposed between anchor mechanism posterior limb inferior surface 141 and spring mechanism superior surface 162.

In one or more embodiments, anchor system 100 may comprise a first elastic band ingress aperture 113. Illustratively, first elastic band ingress aperture 113 may be disposed between elastic band retaining limb 150 and aligner superior interface limb 120, e.g., first elastic band ingress aperture 113 may be disposed between elastic band retaining limb inferior surface 151 and aligner superior interface limb superior surface 122. In one or more embodiments, anchor system 100 may comprise a second elastic band aperture 114. Illustratively, second elastic band aperture 114 may be disposed between elastic band retaining limb 150 and anchor mechanism anterior limb 130, e.g., second elastic band aperture 114 may be disposed between elastic band retaining limb superior surface 152 and anchor mechanism anterior limb inferior surface 131. In one or more embodiments, second elastic band aperture 114 may be disposed between anchor system proximal end 102 and anchor mechanism anterior limb 130, e.g., second elastic band aperture 114 may be disposed between anchor system proximal end 102 and anchor mechanism interior limb inferior surface 131.

Illustratively, anchor system 100 may be manufactured from any suitable material, e.g., polymers, metals, metal alloys, etc., or from any combination of suitable materials. In one or more embodiments, anchor system 100 may be manufactured from spring steel, e.g., anchor system 100 may be manufactured from a shape memory material. In one or more embodiments, anchor system 100 may be manufactured from stainless steel, e.g., anchor system 100 may be manufactured from Type 301 stainless steel, Type 302 stainless steel, Type 303 stainless steel, Type 304 stainless steel, Type 304L stainless steel, Type 304LN stainless steel, Type 310 stainless steel, Type 316 stainless steel, Type 316L stainless steel, Type 316Ti stainless steel, Type 321 stainless steel, Type 430 stainless steel, Type 440 stainless steel, Type 17-7 stainless steel, etc. Illustratively, anchor system 100 may be manufactured from nitinol. In one or more embodiments, anchor system 100 may be manufactured from aluminum, e.g., anchor system 100 may be manufactured from an aluminum alloy. Illustratively, anchor system 100 may be manufactured from a 6061 aluminum alloy, a 6061-T4 aluminum alloy, a 6061-T6 aluminum alloy, a 6063 aluminum alloy, a 6063 aluminum alloy, etc. In one or more embodiments, anchor system 100 may be manufactured from titanium, e.g., anchor system 100 may be manufactured from a titanium alloy. Illustratively, anchor system 100 may be manufactured from a Grade 5 titanium alloy, a Grade 6 titanium alloy, a Grade 7 titanium alloy, a Grade 7H titanium alloy, a Grade 9 titanium alloy, a Grade 11 titanium alloy, a Grade 12 titanium alloy, a Grade 16 titanium alloy, a Grade 17 titanium alloy, a Grade 18 titanium alloy, etc.

In one or more embodiments, a portion of anchor system 100 that may contact a patient's tooth may be manufactured from a material having a hardness of less than 4.2 GPa to prevent the portion of anchor system 100 from damaging the patient's tooth enamel. Illustratively, a portion of anchor system 100 that may contact a patient's tooth may be coated with a material having a hardness of less than 4.2 GPa to prevent the portion of anchor system 100 from damaging the patient's tooth enamel. In one or more embodiments, a portion of anchor system 100 may be manufactured from a material having a hardness in a range of 1.2 to 3.6 GPa to prevent damage to a patient's tooth enamel, e.g., a portion of anchor system 100 may be manufactured from a material having a hardness of 3.5 GPa to prevent damage to a patient's tooth enamel. Illustratively, a portion of anchor system 100 may be covered by a sleeve having a hardness of less than 4.2 GPa configured to prevent damage to a patient's tooth enamel, e.g., aligner inferior interface limb 110 may be covered by a sleeve having a hardness of less than 4.2 GPa. In one or more embodiments, spring mechanism 160 may be covered by a sleeve having a hardness of less than 4.2 GPa configured to prevent damage to a patient's tooth enamel. Illustratively, a portion of anchor system 100 may be wrapped in a cordage having a hardness of less than 4.2 GPa, e.g., a portion of anchor system 100 may be wrapped in a cordage configured to prevent damage to a patient's tooth enamel. In one or more embodiments, a portion of anchor system 100 may be coated by an epoxy having a hardness of less than 4.2 GPa when cured, e.g., a portion of anchor system 100 may be coated by an epoxy configured to prevent damage to a patient's tooth enamel when cured. Illustratively, a portion of anchor system 100 may be electropolished to prevent damage to a patient's tooth enamel.

Figure 2:
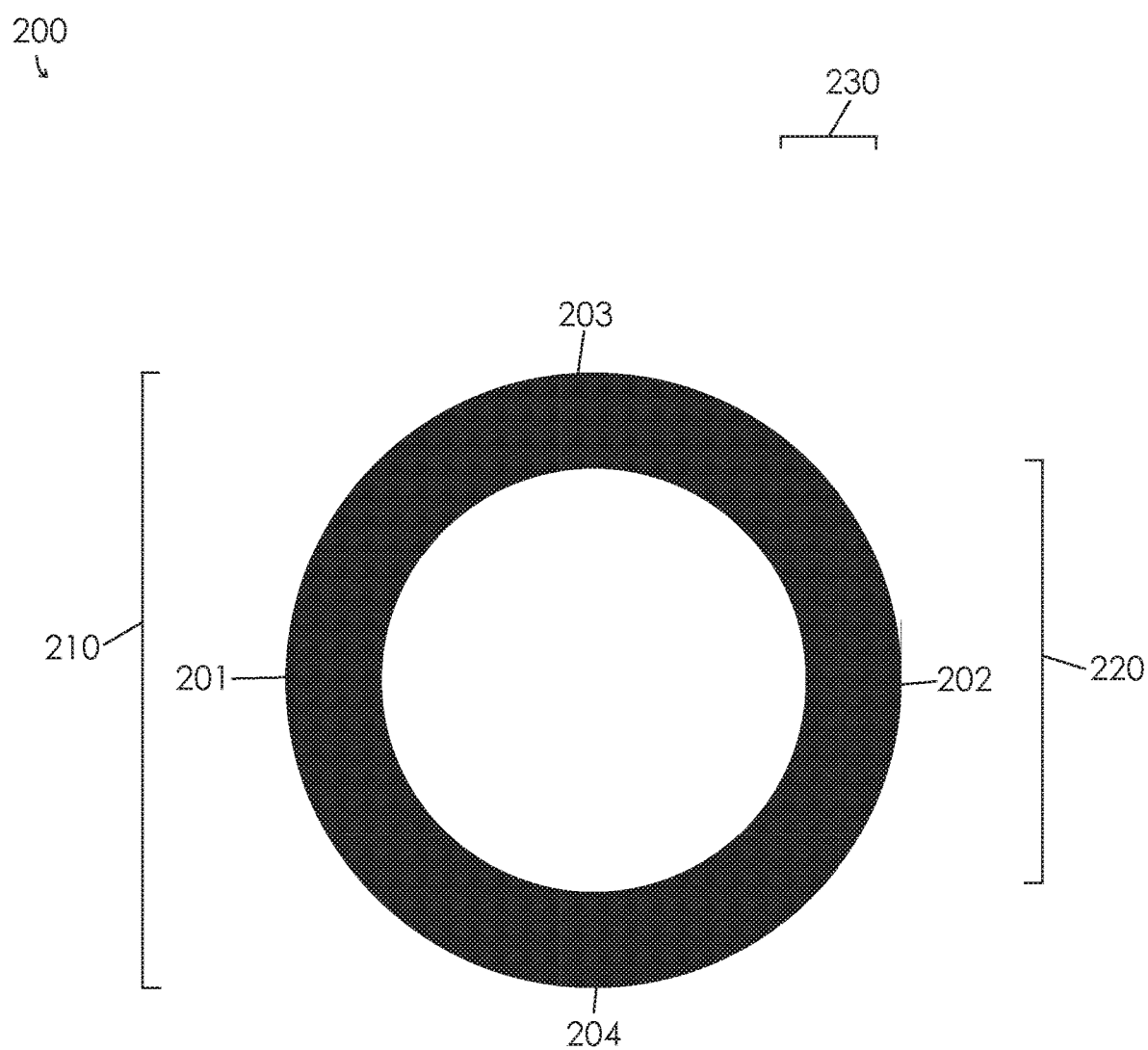
FIG. 2 is a schematic diagram illustrating an elastic band.

FIG. 2 is a schematic diagram illustrating an elastic band 200. Illustratively, an elastic band 200 may comprise an elastic band distal end 201, an elastic band proximal end 202, an elastic band superior end 203, and an elastic band inferior end 204. In one or more embodiments, elastic band 200 may comprise an elastic band outer diameter 210, an elastic band inner diameter 220, and an elastic band width 230. Illustratively, elastic band 200 may comprise an orthodontic elastic, e.g., elastic band 200 may comprise a ligature, an inter-arch elastic, etc.

Figure 3:
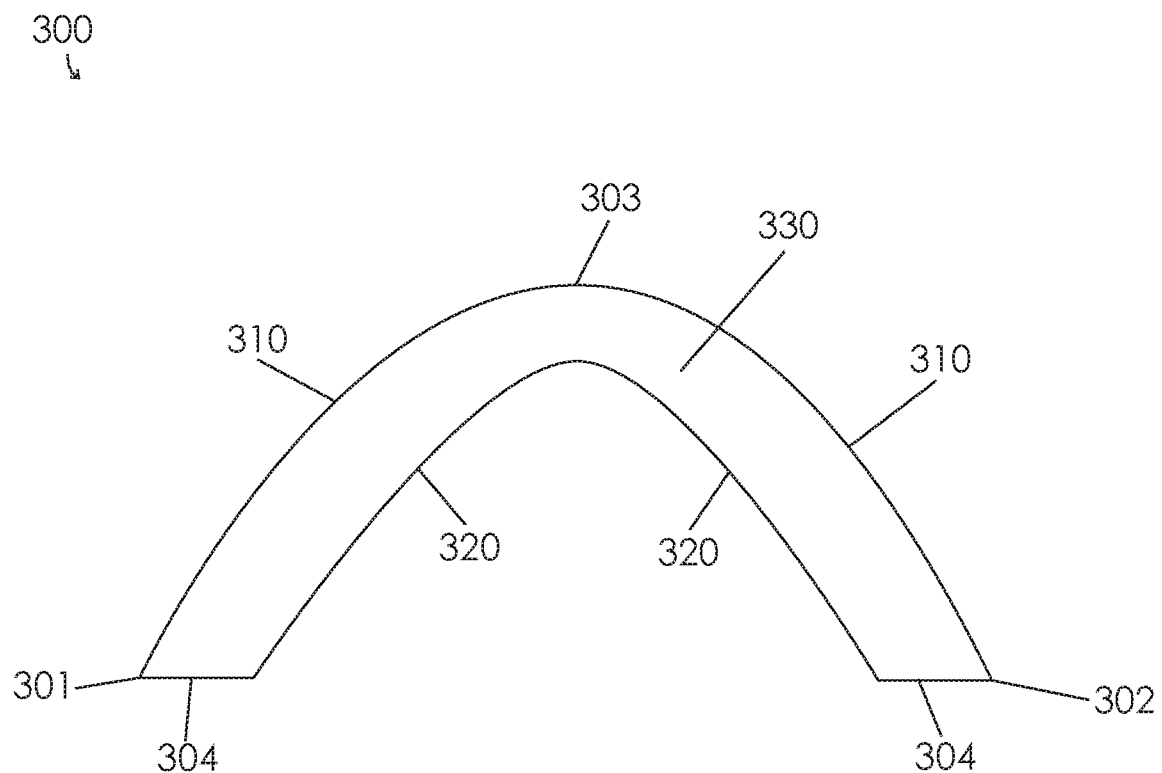
FIG. 3 is a schematic diagram illustrating an aligner.

FIG. 3 is a schematic diagram illustrating an aligner 300. Illustratively, an aligner 300 may comprise an aligner distal end 301, an aligner proximal end 302, an aligner superior end 303, and an aligner inferior end 304. In one or more embodiments, aligner 300 may comprise an aligner lateral margin 310 and an aligner medial margin 320. Illustratively, aligner 300 may comprise a housing for teeth 330, e.g., housing for teeth 330 may be disposed between aligner medial margin 310 and aligner proximal margin 320.

Figure 4A:
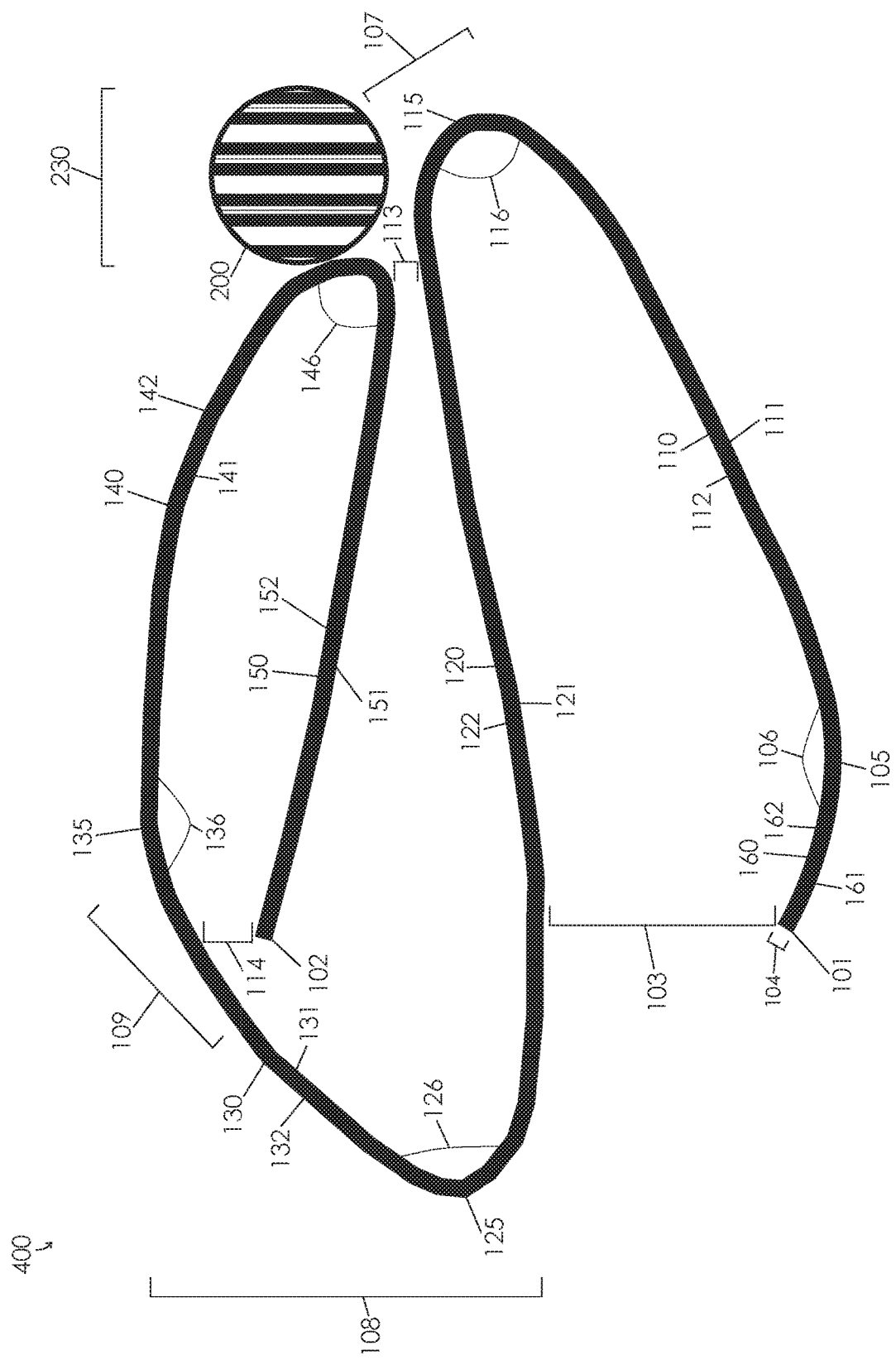
FIGS. 4A, 4B, 4C, and 4D are schematic diagrams illustrating an elastic band attachment.

FIGS. 4A, 4B, 4C, and 4D are schematic diagrams illustrating an elastic band attachment. FIG. 4A illustrates an elastic band oriented for a first anchor system ingress 400. In one or more embodiments, elastic band 200 may comprise an elastic band oriented for a first anchor system ingress 400 when elastic band 200 is actuated towards first elastic band ingress aperture 113, e.g., elastic band 200 may comprise an elastic band oriented for a first anchor system ingress 400 when elastic band outer diameter 210 is actuated towards first elastic band ingress aperture 113. Illustratively, elastic band 200 may be adjacent to fifth joint 145 when elastic band 200 comprises an elastic band oriented for a first anchor system ingress 400.

Figure 4B:
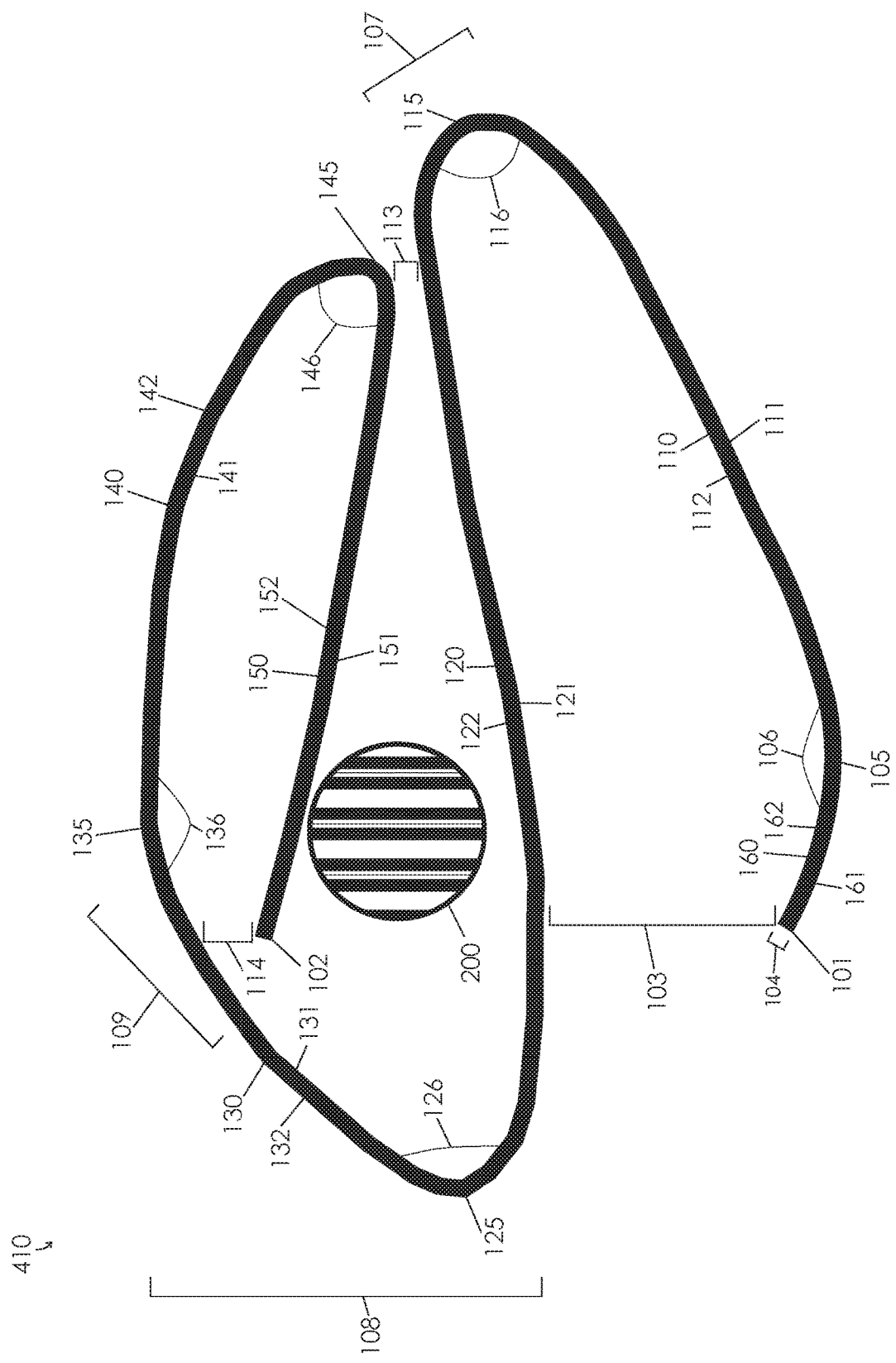

FIG. 4B illustrates a first anchor system ingress 410. In one or more embodiments, actuating elastic band 200 through first elastic band ingress aperture 113 may be configured to dispose elastic band 200 in anchor mechanism 108. Illustratively, an actuation of elastic band 200 through first elastic band ingress aperture 113 may be configured to dispose elastic band 200 between elastic band retaining limb 150 and aligner superior interface limb 120, e.g., an actuation of elastic band 200 through first elastic band ingress aperture 113 may be configured to dispose elastic band 200 between elastic band retaining limb inferior surface 151 and aligner superior interface limb superior surface 122.

Figure 4C:
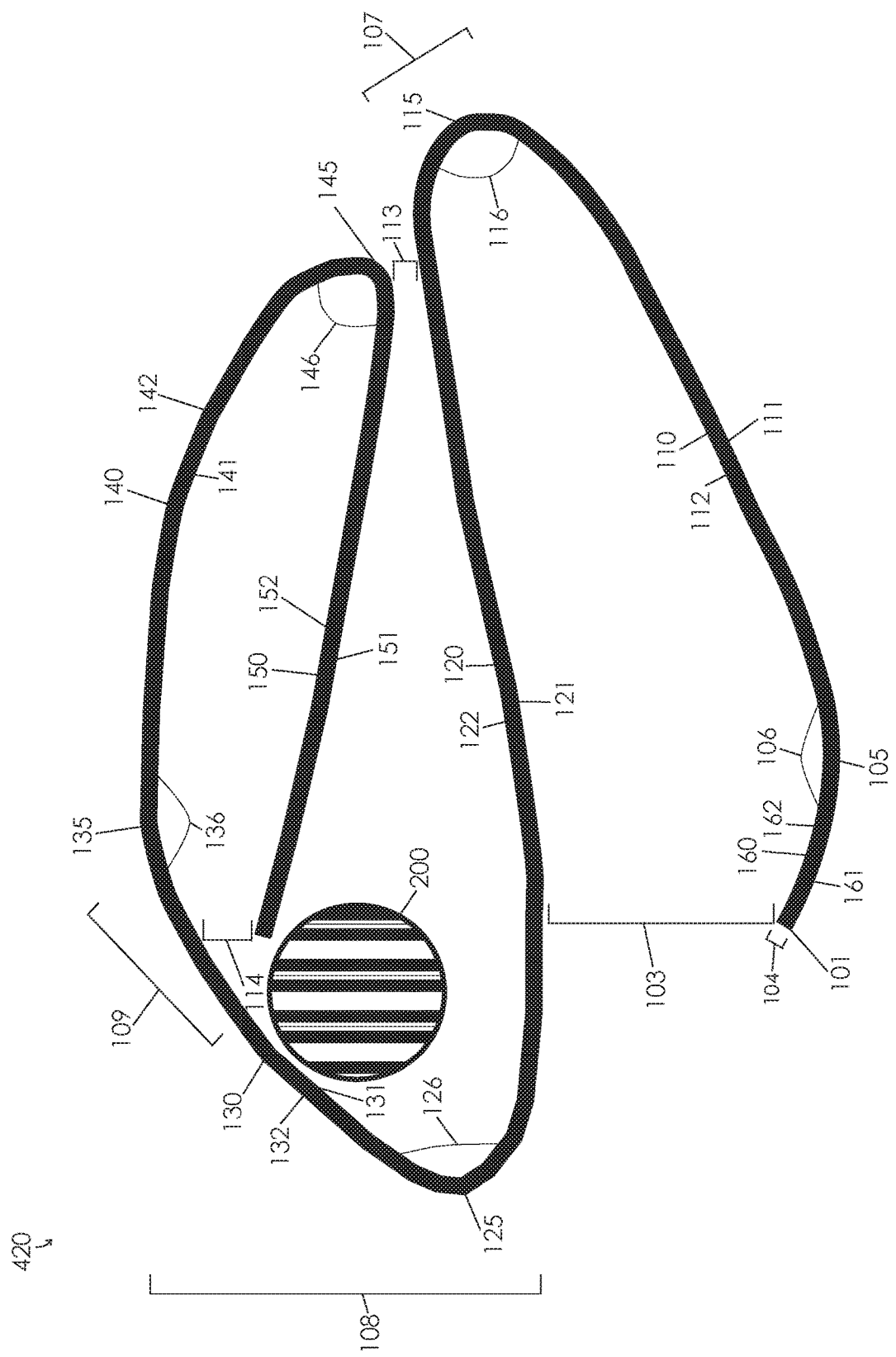

FIG. 4C illustrates an elastic band oriented for a second anchor system ingress 420. In one or more embodiments, elastic band 200 may comprise an elastic band oriented for a second anchor system ingress 420 when elastic band 200 is actuated towards second elastic band ingress aperture 114, e.g., elastic band 200 may comprise an elastic band oriented for a second anchor system ingress 420 when elastic band outer diameter 210 is actuated towards second elastic band ingress aperture 114. Illustratively, a portion of elastic band 200 may be adjacent to a portion of anchor system proximal end 202 when elastic band 200 comprises an elastic band oriented for a second anchor system ingress 420. In one or more embodiments, a portion of elastic band 200 may be adjacent to a portion of anchor mechanism anterior limb 130 when elastic band 200 comprises an elastic band oriented for a second anchor system ingress 420, e.g., a portion of elastic band 200 may be adjacent to a portion of anchor mechanism anterior limb inferior surface 131 when elastic band 200 comprises an elastic band oriented for a second anchor system ingress 420.

Figure 4D:
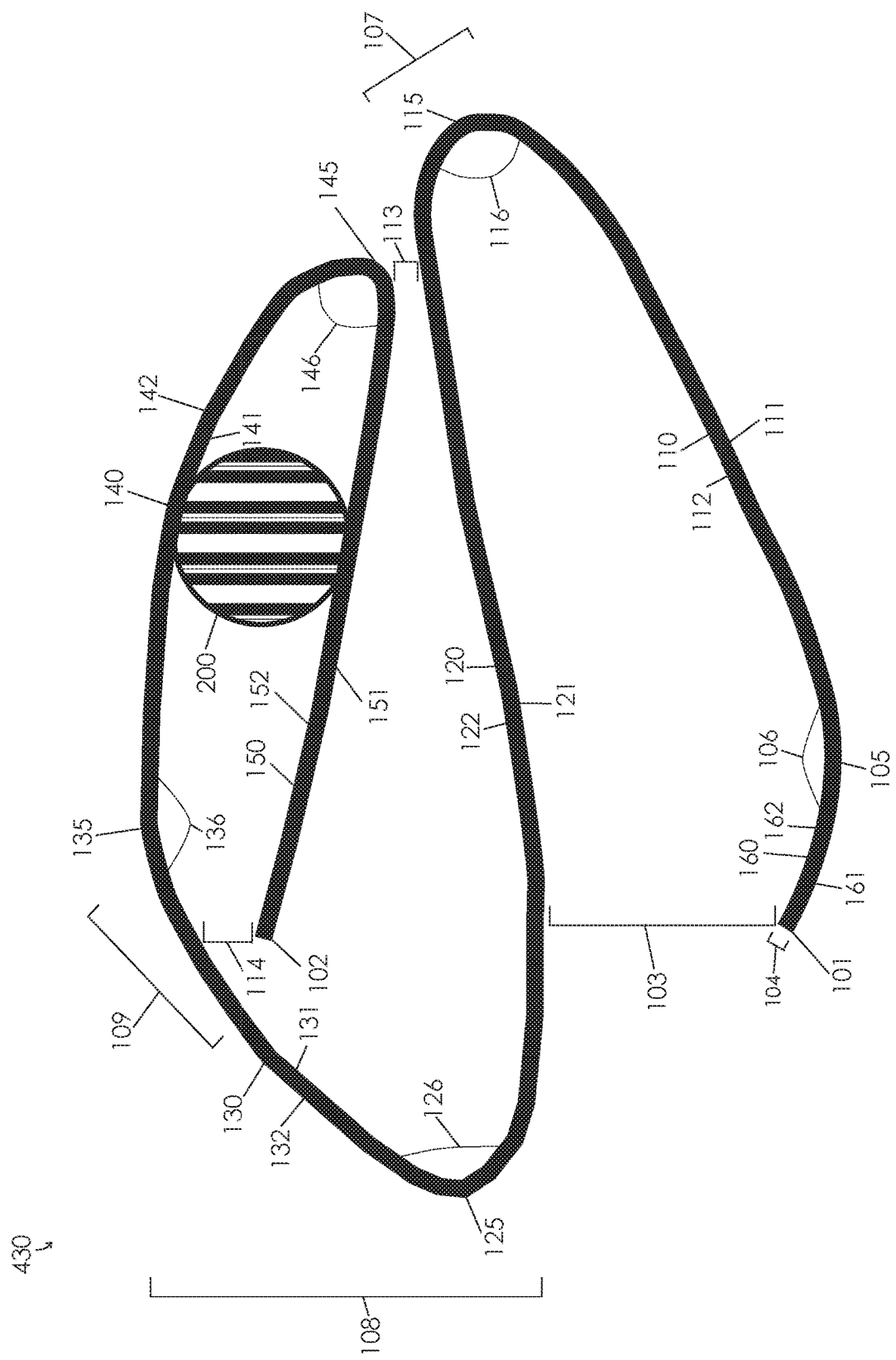

FIG. 4D illustrates a second anchor system ingress 430. In one or more embodiments, actuating elastic band 200 through second elastic band ingress aperture 114 may be configured to dispose elastic band 200 in elastic band receptacle 109. Illustratively, an actuation of elastic band 200 through second elastic band ingress aperture 114 may be configured to dispose elastic band 200 between anchor mechanism posterior limb 140 and elastic band retaining limb 150, e.g., an actuation of elastic band 200 through second elastic band ingress aperture 114 may be configured to dispose elastic band 200 between anchor mechanism posterior limb inferior surface 141 and elastic band retaining limb in superior surface 152. In one or more embodiments, an actuation of elastic band 200 through second elastic band ingress aperture 114 may be configured to dispose elastic band 200 between fourth joint 135 and fifth joint 145. Illustratively, fifth joint angle 146 may be configured to temporarily fix elastic band 200 in elastic band receptacle 109, e.g., fifth joint angle 146 may be configured to temporarily fix elastic band 200 in elastic band receptacle 109 by a force of friction. In one or more embodiments, fifth joint angle 146 may be configured to separate elastic band retaining limb superior surface 152 and anchor mechanism posterior limb inferior surface 141 by a distance that is less than elastic band width 230. Illustratively, fifth joint angle 146 may be increased to correspond to an increased elastic band width 230 of a particular elastic band 200. In one or more embodiments, fifth joint angle 146 may be decreased to correspond to a decreased elastic band width 230 of a particular elastic band 200. Illustratively, a geometry of anchor mechanism posterior limb 140 may be configured to prevent damage to elastic band 200 when elastic band 200 is applying a force to a patient's tooth, e.g., a geometry of anchor mechanism posterior limb inferior surface 141 may be configured to prevent damage to elastic band 200 when elastic band 200 is applying a force to a patient's tooth. In one or more embodiments, a geometry of elastic band retaining limb 150 may be configured to prevent damage to elastic band 200 when elastic band 200 is applying a force to a patient's tooth, e.g., a geometry of elastic band retaining limb superior surface 152 may be configured to prevent damage to elastic band 200 when elastic band 200 is applying a force to a patient's tooth.

Figure 5A:
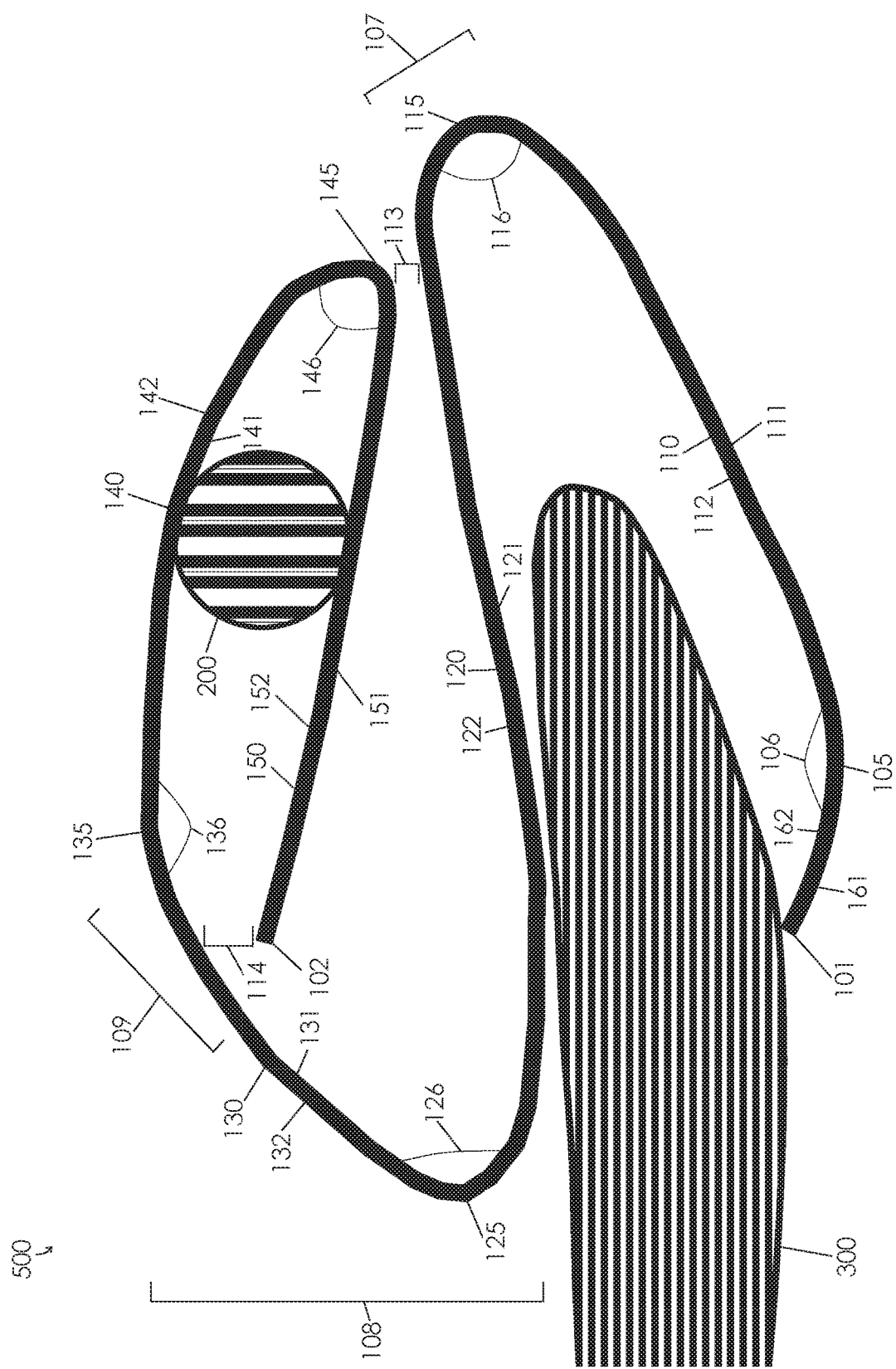
FIGS. 5A, 5B, and 5C are schematic diagrams illustrating an aligner attachment.
Figure 5B:
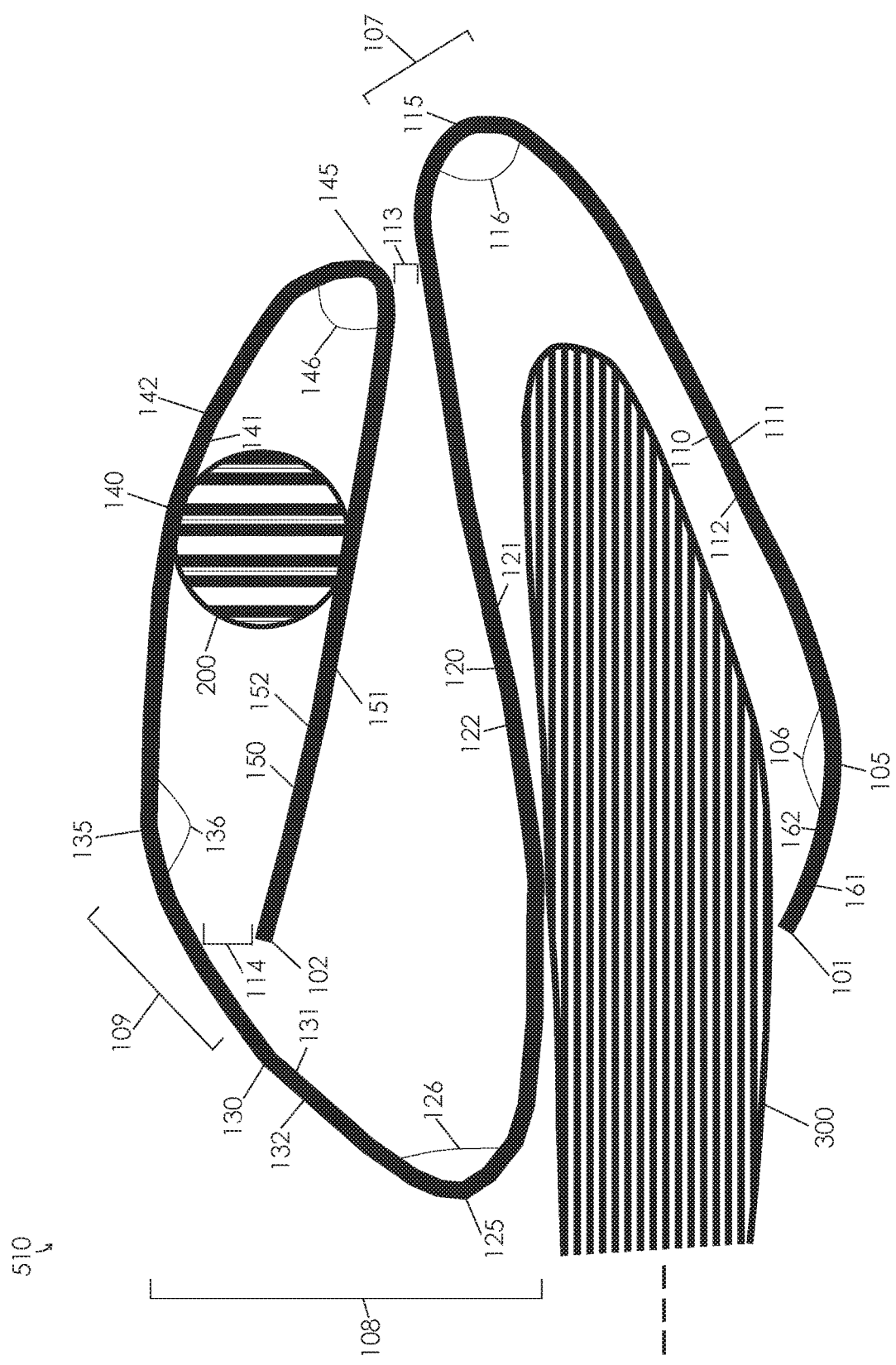
Figure 5C:
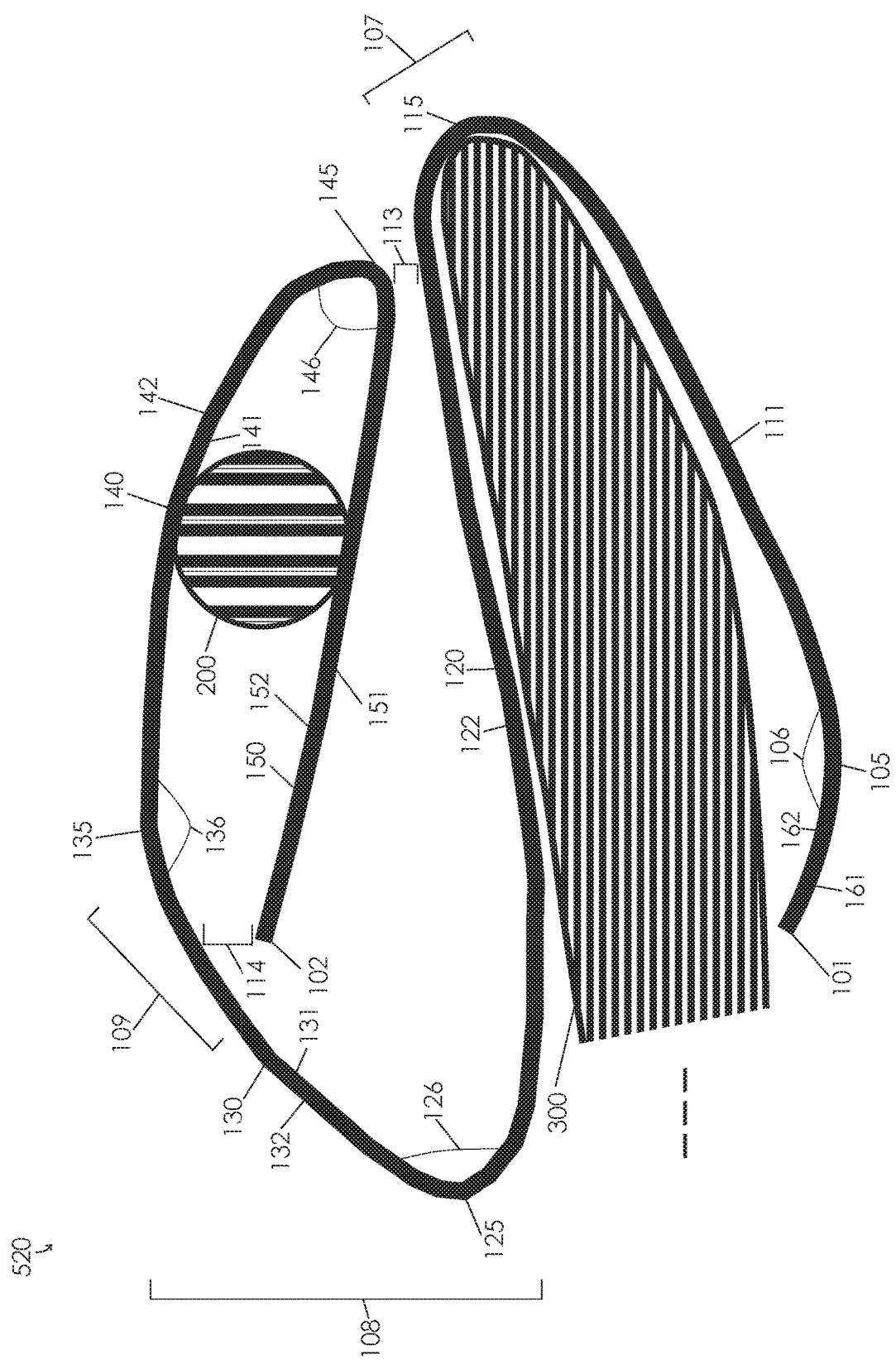

FIGS. 5A, 5B, and 5C are schematic diagrams illustrating an aligner attachment. FIG. 5A illustrates an initiation of an aligner attachment 500. In one or more embodiments, an actuation of a portion of aligner 300 towards a portion of anchor system 100 may comprise an initiation of an aligner attachment 500. Illustratively, an actuation of aligner distal end 301 towards a portion of anchor system 100 may comprise an initiation of an aligner attachment 500. In one or more embodiments, an actuation of aligner proximal end 302 towards a portion of anchor system 100 may comprise an initiation of an aligner attachment 500. Illustratively, an actuation of aligner superior end 303 towards a portion of anchor system 100 may comprise an initiation of an aligner attachment 500. In one or more embodiments, an actuation of aligner inferior end 304 towards a portion of anchor system 100 may comprise an initiation of an aligner attachment 500. Illustratively, an actuation of aligner lateral margin 310 towards a portion of anchor system 100 may comprise an initiation of an aligner attachment 500. In one or more embodiments, an actuation of aligner medial margin 320 towards a portion of anchor system 100 may comprise an initiation of an aligner attachment 500. Illustratively, an actuation of housing for teeth 330 towards a portion of anchor system 100 may comprise an initiation of an aligner attachment 500.

Illustratively, an actuation of a portion of anchor system 100 towards a portion of aligner 300 may comprise an initiation of an aligner attachment 500. In one or more embodiments, an actuation of a portion of anchor system 100 towards aligner distal end 301 may comprise an initiation of an aligner attachment 500. Illustratively, an actuation of a portion of anchor system 100 towards aligner proximal end 302 may comprise an initiation of an aligner attachment 500. In one or more embodiments, an actuation of a portion of anchor system 100 towards aligner superior end 303 may comprise an initiation of an aligner attachment 500. Illustratively, an actuation of a portion of anchor system 100 towards aligner inferior end 304 may comprise an initiation of an aligner attachment 500. In one or more embodiments, an actuation of a portion of anchor system 100 towards aligner lateral margin 310 may comprise an initiation of an aligner attachment 500. Illustratively, an actuation of a portion of anchor system 100 towards aligner medial margin 320 may comprise an initiation of an aligner attachment 500. In one or more embodiments, an actuation of a portion of anchor system 100 towards housing for teeth 330 may comprise an initiation of an aligner attachment 500.

Illustratively, an actuation of a portion of aligner 300 into aligner receptacle 103 may comprise an initiation of an aligner attachment 500. In one or more embodiments, an actuation of aligner distal end 301 into aligner receptacle 103 may comprise an initiation of an aligner attachment 500. Illustratively, an actuation of aligner proximal end 302 into aligner receptacle 103 may comprise an initiation of an aligner attachment 500. In one or more embodiments, an actuation of aligner superior end 303 into aligner receptacle 103 may comprise an initiation of an aligner attachment 500. Illustratively, an actuation of aligner inferior end 304 into aligner receptacle 103 may comprise an initiation of an aligner attachment 500. In one or more embodiments, an actuation of aligner lateral margin 310 into aligner receptacle 103 may comprise an initiation of an aligner attachment 500. Illustratively, an actuation of aligner medial margin 320 into aligner receptacle 103 may comprise an initiation of an aligner attachment 500. In one or more embodiments, an actuation of housing for teeth 330 into aligner receptacle 103 may comprise an initiation of an aligner attachment 500.

Illustratively, an actuation of a portion of aligner 300 towards aligner receptacle 103 may comprise an initiation of an aligner attachment 500. In one or more embodiments, an actuation of aligner distal end 301 towards aligner receptacle 103 may comprise an initiation of an aligner attachment 500. Illustratively, an actuation of aligner proximal end 302 towards aligner receptacle 103 may comprise an initiation of an aligner attachment 500. In one or more embodiments, an actuation of aligner superior end 303 towards aligner receptacle 103 may comprise an initiation of an aligner attachment 500. Illustratively, an actuation of aligner inferior end 304 towards aligner receptacle 103 may comprise an initiation of an aligner attachment 500. In one or more embodiments, an actuation of aligner lateral margin 310 towards aligner receptacle 103 may comprise an initiation of an aligner attachment 500. Illustratively, an actuation of aligner medial margin 320 towards aligner receptacle 103 may comprise an initiation of an aligner attachment 500. In one or more embodiments, an actuation of housing for teeth 330 towards aligner receptacle 103 may comprise an initiation of an aligner attachment 500.

Illustratively, an actuation of a portion of aligner 300 towards aligner housing 107 may be comprise an initiation of an aligner attachment 500. In one or more embodiments, an actuation of aligner distal end 301 towards aligner housing 107 may be comprise an initiation of an aligner attachment 500. Illustratively, an actuation of aligner proximal end 302 towards aligner housing 107 may be comprise an initiation of an aligner attachment 500. In one or more embodiments, an actuation of aligner superior end 303 towards aligner housing 107 may be comprise an initiation of an aligner attachment 500. Illustratively, an actuation of aligner inferior end 304 towards aligner housing 107 may be comprise an initiation of an aligner attachment 500. In one or more embodiments, an actuation of aligner lateral margin 310 towards aligner housing 107 may be comprise an initiation of an aligner attachment 500. Illustratively, an actuation of aligner medial margin 320 towards aligner housing 107 may be comprise an initiation of an aligner attachment 500. In one or more embodiments, an actuation of housing for teeth 330 towards aligner housing 107 may be comprise an initiation of an aligner attachment 500.

Illustratively, an actuation of a portion of aligner 300 towards second joint 115 may comprise an initiation of an aligner attachment 500. In one or more embodiments, an actuation of aligner distal end 301 towards second joint 115 may comprise an initiation of an aligner attachment 500. Illustratively, an actuation of aligner proximal end 302 towards second joint 115 may comprise an initiation of an aligner attachment 500. In one or more embodiments, an actuation of aligner superior end 303 towards second joint 115 may comprise an initiation of an aligner attachment 500. Illustratively, an actuation of aligner inferior end 304 towards second joint 115 may comprise an initiation of an aligner attachment 500. In one or more embodiments, an actuation of aligner lateral margin 310 towards second joint 115 may comprise an initiation of an aligner attachment 500. Illustratively, an actuation of aligner medial margin 320 towards second joint 115 may comprise an initiation of an aligner attachment 500. In one or more embodiments, an actualion of housing for teeth 330 towards second joint 115 may comprise an initiation of an aligner attachment 500.

In one or more embodiments, elastic band 200 may be disposed in elastic band receptacle 109 before an initiation of an aligner attachment 500, e.g., elastic band 200 may be actuated into elastic band receptacle 109 before an initiation of an aligner attachment 500. Illustratively, elastic band 200 may not be disposed in elastic band receptacle 109 before an initiation of an aligner attachment 500, e.g., elastic band 200 may be actuated into elastic band receptacle 109 after an initiation of an aligner attachment 500.

FIG. 5B illustrates a partial aligner attachment 510. In one or more embodiments, after an initiation of an aligner attachment 500, an actuation of a portion of aligner 300 towards second joint 115 may comprise a partial aligner attachment 510. Illustratively, after an initiation of an aligner attachment 500, an actuation of aligner distal end 301 towards second joint 115 may comprise a partial aligner attachment 510. In one or more embodiments, after an initiation of an aligner attachment 500, an actuation of aligner proximal end 302 towards second joint 115 may comprise a partial aligner attachment 510. Illustratively, after an initiation of an aligner attachment 500, an actuation of aligner superior end 303 towards second joint 115 may comprise a partial aligner attachment 510. In one or more embodiments, after an initiation of an aligner attachment 500, an actuation of aligner inferior end 304 towards second joint 115 may comprise a partial aligner attachment 510. Illustratively, after an initiation of an aligner attachment 500, an actuation of aligner lateral margin 310 towards second joint 115 may comprise a partial aligner attachment 510. In one or more embodiments, after an initiation of an aligner attachment 500, an actuation of aligner medial margin 320 towards second joint 115 may comprise a partial aligner attachment 510. Illustratively, after an initiation of an aligner attachment 500, an actuation of housing for teeth 330 towards second joint 115 may comprise a partial aligner attachment 510.

In one or more embodiments, after an initiation of an aligner attachment 500, an actuation of a portion of anchor system 100 over a portion of aligner 300 may comprise a partial aligner attachment 510. Illustratively, after an initiation of an aligner attachment 500, an actuation of a portion of anchor system 100 over aligner distal end 301 may comprise a partial aligner attachment 510. In one or more embodiments, after an initiation of an aligner attachment 500, an actuation of a portion of anchor system 100 over aligner proximal end 302 may comprise a partial aligner attachment 510. Illustratively, after an initiation of an aligner attachment 500, an actuation of a portion of anchor system 100 over aligner superior end 303 may comprise a partial aligner attachment 510. In one or more embodiments, after an initiation of an aligner attachment 500, an actuation of a portion of anchor system 100 over aligner inferior end 304 may comprise a partial aligner attachment 510. Illustratively, after an initiation of an aligner attachment 500, an actuation of a portion of anchor system 100 over aligner lateral margin 310 may comprise a partial aligner attachment 510. In one or more embodiments, after an initiation of an aligner attachment 500, an actuation of a portion of anchor system 100 over aligner median margin 320 may comprise a partial aligner attachment 510. Illustratively, after an initiation of an aligner attachment 500, an actuation of a portion of anchor system 100 over housing for teeth 330 may comprise a partial aligner attachment 510.

In one or more embodiments, after an initiation of an aligner attachment 500, an actuation of a portion of aligner 300 through aligner receptacle 103 may comprise a partial aligner attachment 510. Illustratively, after an initiation of an aligner attachment 500, an actuation of aligner distal end 301 through aligner receptacle 103 may comprise a partial aligner attachment 510. In one or more embodiments, after an initiation of an aligner attachment 500, an actuation of aligner proximal end 302 through aligner receptacle 103 may comprise a partial aligner attachment 510. Illustratively, after an initiation of an aligner attachment 500, an actuation of aligner superior end 303 through aligner receptacle 103 may comprise a partial alignerattachment 510. In one or more embodiments, after an initiation of an aligner attachment 500, an actuation of aligner inferior end 304 through aligner receptacle 103 may comprise a partial aligner attachment 510. Illustratively, after an initiation of an aligner attachment 500, an actuation of aligner lateral margin 310 through aligner receptacle 103 may comprise a partial aligner attachment 510. In one or more embodiments, after an initiation of an aligner attachment 500, an actuation of aligner medial margin 320 through aligner receptacle 103 may comprise a partial aligner attachment 510. Illustratively, after an initiation of an aligner attachment 500, an actuation of housing for teeth 330 through aligner receptacle 103 may comprise a partial aligner attachment 510.

In one or more embodiments, a partial actuation of a portion of aligner 300 into aligner housing 107 may comprise a partial aligner attachment 510. Illustratively, a partial actuation of a portion of aligner distal end 301 into aligner housing 107 may comprise a partial aligner attachment 510. In one or more embodiments, a partial actuation of a portion of aligner proximal end 302 into aligner housing 107 may comprise a partial aligner attachment 510. Illustratively, a partial actuation of a portion of aligner superior end 303 into aligner housing 107 may comprise a partial aligner attachment 510. In one or more embodiments, a partial actuation of a portion of aligner inferior end 304 into aligner housing 107 may comprise a partial aligner attachment 510. Illustratively, a partial actuation of a portion of aligner lateral margin 310 into aligner housing 107 may comprise a partial aligner attachment 510. In one or more embodiments, a partial actuation of a portion of aligner medial margin 320 into aligner housing 107 may comprise a partial aligner attachment 510. Illustratively, a partial actuation of a portion of housing for teeth 330 into aligner housing 107 may comprise a partial aligner attachment 510.

In one or more embodiments, disposing a portion of aligner 300 between aligner superior interface limb 120 and aligner inferior interface limb 110 may comprise a partial aligner attachment 510, e.g., disposing a portion of aligner 300 between aligner superior interface limb inferior surface 121 and aligner inferior interface limb superior surface 112 may comprise a partial aligner attachment 510. Illustratively, disposing a portion of aligner distal end 301 between aligner superior interface limb 120 and aligner inferior interface limb 110 may comprise a partial aligner attachment 510, e.g., disposing a portion of aligner distal end 301 between aligner superior interface limb inferior surface 121 and aligner inferior interface limb superior surface 112 may comprise a partial aligner attachment 510. In one or more embodiments, disposing a portion of aligner proximal end 302 between aligner superior interface limb 120 and aligner inferior interface limb 110 may comprise a partial aligner attachment 510, e.g., disposing a portion of aligner proximal end 302 between aligner superior interface limb inferior surface 121 and aligner inferior interface limb superior surface 112 may comprise a partial aligner attachment 510. Illustratively, disposing a portion of aligner superior end 303 between aligner superior interface limb 120 and aligner inferior interface limb 110 may comprise a partial aligner attachment 510, e.g., disposing a portion of aligner superior end 303 between aligner superior interface limb inferior surface 121 and aligner inferior interface limb superior surface 112 may comprise a partial aligner attachment 510. In one or more embodiments, disposing a portion of aligner inferior end 304 between aligner superior interface limb 120 and aligner inferior interface limb 110 may comprise a partial aligner attachment 510, e.g., disposing a portion of aligner inferior end 304 between aligner superior interface limb inferior surface 121 and aligner inferior interface limb superior surface 112 may comprise a partial aligner attachment 510. Illustratively, disposing a portion of aligner lateral margin 310 between aligner superior interface limb 120 and aligner inferior interface limb 110 may comprise a partial aligner attachment 510, e.g., disposing a portion of aligner lateral margin 310 between aligner superior interface limb inferior surface 121 and aligner inferior interface limb superior surface 112 may comprise a partial aligner attachment 510. In one or more embodiments, disposing a portion of aligner medial margin 320 between aligner superior interface limb 120 and aligner inferior interface limb 110 may comprise a partial aligner attachment 510, e.g., disposing a portion of aligner medial margin 320 between aligner superior interface limb inferior surface 121 and aligner inferior interface limb superior surface 112 may comprise a partial aligner attachment 510. Illustratively, disposing a portion of housing for teeth 330 between aligner superior interface limb 120 and aligner inferior interface limb 110 may comprise a partial aligner attachment 510, e.g., disposing a portion of housing for teeth 330 between aligner superior interface limb inferior surface 121 and aligner inferior interface limb superior surface 112 may comprise a partial aligner attachment 510.

FIG. 5C illustrates a complete aligner attachment 520. In one or more embodiments, after a partial aligner attachment 510, an actuation of a portion of aligner 300 towards second joint 115 may comprise a complete aligner attachment 520. Illustratively, after a partial aligner attachment 510, an actuation of aligner distal end 301 towards second joint 115 may comprise a complete aligner attachment 520. In one or more embodiments, after a partial aligner attachment 510, an actuation of aligner proximal end 302 towards second joint 115 may comprise a complete aligner attachment 520. Illustratively, after a partial aligner attachment 510, an actuation of aligner superior end 303 towards second joint 115 may comprise a complete aligner attachment 520. In one or more embodiments, after a partial aligner attachment 510, an actuation of aligner inferior end 304 towards second joint 115 may comprise a complete aligner attachment 520. Illustratively, after a partial aligner attachment 510, an actuation of aligner lateral margin 310 towards second joint 115 may comprise a complete aligner attachment 520. In one or more embodiments, after a partial aligner attachment 510, an actuation of aligner medial margin 320 towards second joint 115 may comprise a complete aligner attachment 520. Illustratively, after a partial aligner attachment 510, an actuation of housing for teeth 330 towards second joint 115 may comprise a complete aligner attachment 520.

In one or more embodiments, after a partial aligner attachment 510, an actuation of a portion of anchor system 100 over a portion of aligner 300 may comprise a complete aligner attachment 520. Illustratively, after a partial aligner attachment 510, an actuation of a portion of anchor system 100 over a portion of aligner distal end 310 may comprise a complete aligner attachment 520. In one or more embodiments, after a partial aligner attachment 510, an actuation of a portion of anchor system 100 over a portion of aligner proximal end 302 may comprise a complete aligner attachment 520. Illustratively, after a partial aligner attachment 510, an actuation of a portion of anchor system 100 over a portion of aligner superior end 303 may comprise a complete aligner attachment 520. In one or more embodiments, after a partial aligner attachment 510, an actuation of a portion of anchor system 100 over a portion of aligner inferior end 304 may comprise a complete aligner attachment 520. Illustratively, after a partial aligner attachment 510, an actuation of a portion of anchor system 100 over a portion of aligner lateral margin 310 may comprise a complete aligner attachment 520. In one or more embodiments, after a partial aligner attachment 510, an actuation of a portion of anchor system 100 over a portion of aligner medial margin 320 may comprise a complete aligner attachment 520. Illustratively, after a partial aligner attachment 510, an actuation of a portion of anchor system 100 over a portion of housing for teeth 330 may comprise a complete aligner attachment 520.

In one or more embodiments, a complete actuation of a portion of aligner 300 into aligner housing 107 may comprise a complete aligner attachment 520. Illustratively, a complete actuation of a portion of aligner distal end 301 into aligner housing 107 may comprise a complete aligner attachment 520. In one or more embodiments, a complete actuation of a portion of aligner proximal end 302 into aligner housing 107 may comprise a complete aligner attachment 520. Illustratively, a complete actuation of a portion of aligner superior end 303 into aligner housing 107 may comprise a complete aligner attachment 520. In one or more embodiments, a complete actuation of a portion of aligner inferior end 304 into aligner housing 107 may comprise a complete aligner attachment 520. Illustratively, a complete actuation of a portion of aligner lateral margin 310 into aligner housing 107 may comprise a complete aligner attachment 520. In one or more embodiments, a complete actuation of a portion of aligner medial margin 320 into aligner housing 107 may comprise a complete aligner attachment 520. Illustratively, a complete actuation of a portion of housing for teeth 330 into aligner housing 107 may comprise a complete aligner attachment 520.

In one or more embodiments, a portion of aligner 300 may be adjacent to second joint 115 when the portion of aligner 300 is completely actuated into aligner housing 107, e.g., a portion of aligner 300 may abut second joint 115 when the portion of aligner 300 is completely actuated into aligner housing 107. Illustratively, a portion of aligner distal end 301 may be adjacent to second joint 115 when the portion of aligner distal end 301 is completely actuated into aligner housing 107, e.g., a portion of aligner distal end 301 may abut second joint 115 when the portion of aligner distal end 301 is completely actuated into aligner housing 107. In one or more embodiments, a portion of aligner proximal end 302 may be adjacent to second joint 115 when the portion of aligner proximal end 302 is completely actuated into aligner housing 107, e.g., a portion of aligner proximal end 302 may abut second joint 115 when the portion of aligner proximal end 302 is completely actuated into aligner housing 107. Illustratively, a portion of aligner superior end 303 may be adjacent to second joint 115 when the portion of aligner superior end 303 is completely actuated into aligner housing 107, e.g., a portion of aligner superior end 303 may abut second joint 115 when the portion of aligner superior end 303 is completely actuated into aligner housing 107. In one or more embodiments, a portion of aligner inferior end 304 may be adjacent to second joint 115 when the portion of aligner inferior end 304 is completely actuated into aligner housing 107, e.g., a portion of aligner inferior end 304 may abut second joint 115 when the portion of aligner inferior end 304 is completely actuated into aligner housing 107. Illustratively, a portion of aligner lateral margin 310 may be adjacent to second joint 115 when the portion of aligner lateral margin 310 is completely actuated into aligner housing 107, e.g., a portion of aligner lateral margin 310 may abut second joint 115 when the portion of aligner lateral margin 310 is completely actuated into aligner housing 107. In one or more embodiments, a portion of aligner meal margin 320 may be adjacent to second joint 115 when the portion of aligner medial margin 320 is completely actuated into aligner housing 107, e.g., a portion of aligner medial margin 320 may abut second joint 115 when the portion of aligner medial margin 320 is completely actuated into aligner housing 107. Illustratively, a portion of housing for teeth 330 may be adjacent to second joint 115 when the portion of housing for teeth 330 is completely actuated into aligner housing 107, e.g., a portion of housing for teeth 330 may abut second joint 115 when the portion of housing for teeth 330 is completely actuated into aligner housing 107.

In one or more embodiments, a portion of aligner 300 may be adjacent to aligner superior interface limb 120 when the portion of aligner 300 is completely actuated into aligner housing 107, e.g., a portion of aligner 300 may abut aligner superior interface limb inferior surface 121 when the portion of aligner 300 is completely actuated into aligner housing 107. Illustratively, a portion of aligner distal end 301 may be adjacent to aligner superior interface limb 120 when the portion of aligner distal end 301 is completely actuated into aligner housing 107, e.g., a portion of aligner distal end 301 may abut aligner superior interface limb inferior surface 121 when the portion of aligner distal end 301 is completely actuated into aligner housing 107. In one or more embodiments, a portion of aligner proximal end 302 may be adjacent to aligner superior interface limb 120 when the portion of aligner proximal end 302 is completely actuated into aligner housing 107, e.g., a portion of aligner proximal end 302 may abut aligner superior interface limb inferior surface 121 when the portion of aligner proximal end 302 is completely actuated into aligner housing 107. Illustratively, a portion of aligner superior end 303 may be adjacent to aligner superior interface limb 120 when the portion of aligner superior end 303 is completely actuated into aligner housing 107, e.g., a portion of aligner superior end 303 may abut aligner superior interface limb inferior surface 121 when the portion of aligner superior end 303 is completely actuated into aligner housing 107. In one or more embodiments, a portion of aligner inferior end 304 may be adjacent to aligner superior interface limb 120 when the portion of aligner inferior end 304 is completely actuated into aligner housing 107, e.g., a portion of aligner inferior end 304 may abut aligner superior interface limb inferior surface 121 when the portion of aligner inferior end 304 is completely actuated into aligner housing 107. Illustratively, a portion of aligner lateral margin 310 may be adjacent to aligner superior interface limb 120 when the portion of aligner lateral margin 310 is completely actuated into aligner housing 107, e.g., a portion of aligner lateral margin 310 may abut aligner superior interface limb inferior surface 121 when the portion of aligner lateral margin 310 is completely actuated into aligner housing 107. In one or more embodiments, a portion of aligner medial margin 320 may be adjacent to aligner superior interface limb 120 when the portion of aligner medial margin 320 is completely actuated into aligner housing 107, e.g., a portion of aligner medial margin 320 may abut aligner superior interface limb inferior surface 121 when the portion of aligner medial margin 320 is completely actuated into aligner housing 107. Illustratively, a portion of housing for teeth 330 may be adjacent to aligner superior interface limb 120 when the portion of housing for teeth 330 is completely actuated into aligner housing 107, e.g., a portion of housing for teeth 330 may abut aligner superior interface limb inferior surface 121 when the portion of housing for teeth 330 is completely actuated into aligner housing 107.

In one or more embodiments, a portion of aligner 300 may be adjacent to aligner inferior interface limb 110 when the portion of aligner 300 is completely actuated into aligner housing 107, e.g., a portion of aligner 300 may abut aligner inferior interface limb superior surface 111 when the portion of aligner 300 is completely actuated into aligner housing 107. Illustratively, a portion of aligner distal end 301 may be adjacent to aligner inferior interface limb 110 when the portion of aligner distal end 301 is completely actuated into aligner housing 107, e.g., a portion of aligner distal end 301 may abut aligner inferior interface limb superior surface 111 when the portion of aligner distal end 301 is completely actuated into aligner housing 107. In one or more embodiments, a portion of aligner proximal end 302 may be adjacent to aligner inferior interface limb 110 when the portion of aligner proximal end 302 is completely actuated into aligner housing 107, e.g., a portion of aligner proximal end 302 may abut aligner inferior interface limb superior surface 111 when the portion of aligner proximal end 302 is completely actuated into aligner housing 107. Illustratively, a portion of aligner superior end 303 may be adjacent to aligner inferior interface limb 110 when the portion of aligner superior end 303 is completely actuated into aligner housing 107, e.g., a portion of aligner superior end 303 may abut aligner inferior interface limb superior surface 111 when the portion of superior end 303 is completely actuated into aligner housing 107. In one or more embodiments, a portion of aligner inferior end 304 may be adjacent to aligner inferior interface limb 110 when the portion of aligner inferior end 304 is completely actuated into aligner housing 107, e.g., a portion of aligner inferior end 304 may abut aligner inferior interface limb superior surface 111 when the portion of aligner inferior end 304 is completely actuated into aligner housing 107. Illustratively, a portion of aligner lateral margin 310 may be adjacent to aligner inferior interface limb 110 when the portion of aligner lateral margin 310 is completely actuated into aligner housing 107, e.g., a portion of aligner lateral margin 310 may abut aligner inferior interface limb superior surface 111 when the portion of aligner lateral margin 310 is completely actuated into aligner housing 107. In one or more embodiments, a portion of aligner medial margin 320 may be adjacent to aligner inferior interface limb 110 when the portion of aligner medial margin 320 is completely actuated into aligner housing 107, e.g., a portion of aligner medial margin 320 may abut aligner inferior interface limb superior surface 111 when the portion of aligner medial margin 320 is completely actuated into aligner housing 107. Illustratively, a portion of housing for teeth 330 may be adjacent to aligner inferior interface limb 110 when the portion of housing for teeth 330 is completely actuated into aligner housing 107, e.g., a portion of housing for teeth 330 may abut aligner inferior interface limb superior surface 111 when the portion of housing for teeth 330 is completely actuated into aligner housing 107.

In one or more embodiments, a portion of aligner 300 may be adjacent to spring mechanism 160 when the portion of aligner 300 is completely actuated into aligner housing 107, e.g., a portion of aligner 300 may abut spring mechanism superior surface 162 when the portion of aligner 300 is completely actuated into aligner housing 107. Illustratively, a portion of aligner distal end 301 may be adjacent to spring mechanism 160 when the portion of aligner distal end 301 is completely actuated into aligner housing 107, e.g., a portion of aligner distal end 301 may abut spring mechanism superior surface 162 when the portion of aligner distal end 301 is completely actuated into aligner housing 107. In one or more embodiments, a portion of aligner proximal end 302 may be adjacent to spring mechanism 160 when the portion of aligner proximal end 302 is completely actuated into aligner housing 107, e.g., a portion of aligner proximal end 302 may abut spring mechanism superior surface 162 when the portion of aligner proximal end 302 is completely actuated into aligner housing 107. Illustratively, a portion of aligner superior end 303 may be adjacent to spring mechanism 160 when the portion of aligner superior end 303 is completely actuated into aligner housing 107, e.g., a portion of aligner superior end 303 may abut spring mechanism superior surface 162 when the portion of aligner superior end 303 is completely actuated into aligner housing 107. In one or more embodiments, a portion of aligner inferior end 304 may be adjacent to spring mechanism 160 when the portion of aligner inferior end 304 is completely actuated into aligner housing 107, e.g., a portion of aligner inferior end 304 may abut spring mechanism superior surface 162 when the portion of aligner inferior end 304 is completely actuated into aligner housing 107. Illustratively, a portion of aligner lateral margin 310 may be adjacent to spring mechanism 160 when the portion of aligner lateral margin 310 is completely actuated into aligner housing 107, e.g., a portion of aligner lateral margin 310 may abut spring mechanism superior surface 162 when the portion of aligner lateral margin 310 is completely actuated into aligner housing 107. In one or more embodiments, a portion of aligner medial margin 320 may be adjacent to spring mechanism 160 when the portion of aligner medial margin 320 is completely actuated into aligner housing 107, e.g., a portion of aligner medial margin 320 may abut spring mechanism superior surface 162 when the portion of aligner medial margin 320 is completely actuated into aligner housing 107. Illustratively, a portion of housing for teeth 330 may be adjacent to spring mechanism 160 when the portion of housing for teeth 330 is completely actuated into aligner housing 107, e.g., a portion of housing for teeth 330 may abut spring mechanism superior surface 162 when the portion of housing for teeth 330 is completely actuated into aligner housing 107.

In one or more embodiments, spring mechanism 160 may be configured to apply a force to a portion of aligner 300, e.g., spring mechanism 160 may be configured to apply a force to a portion of aligner 300 to maintain a complete aligner attachment 520. Illustratively, spring mechanism 160 may be configured to apply a force to a portion of aligner 300 having a magnitude in a range of 0.36 to 1.33 N, e.g., spring mechanism 160 may be configured to apply a force to a portion of aligner 300 having a magnitude of 1.12 N. In one or more embodiments, spring mechanism 160 may be configured to apply a force to a portion of aligner 300 having a magnitude of less than 0.36 N or greater than 1.33 N. Illustratively, elastic band retaining limb 150 may be configured to apply a force to a portion of elastic band 200, e.g., elastic band retaining limb 150 may be configured to apply a force to a portion of elastic band 200 to maintain a second anchor system ingress 430. In one or more embodiments, elastic band retaining limb 150 may be configured to apply a force to a portion of elastic band 200 having a magnitude in a range of 0.76 to 16.66 N, e.g., elastic band retaining limb 150 may be configured to apply a force to a portion of elastic band 200 having a magnitude of 11.53 N. Illustratively, elastic band retaining limb 150 may be configured to apply a force to a portion of elastic band 200 having a magnitude of less than 0.76 N or greater than 16.66 N.

Figure 6:
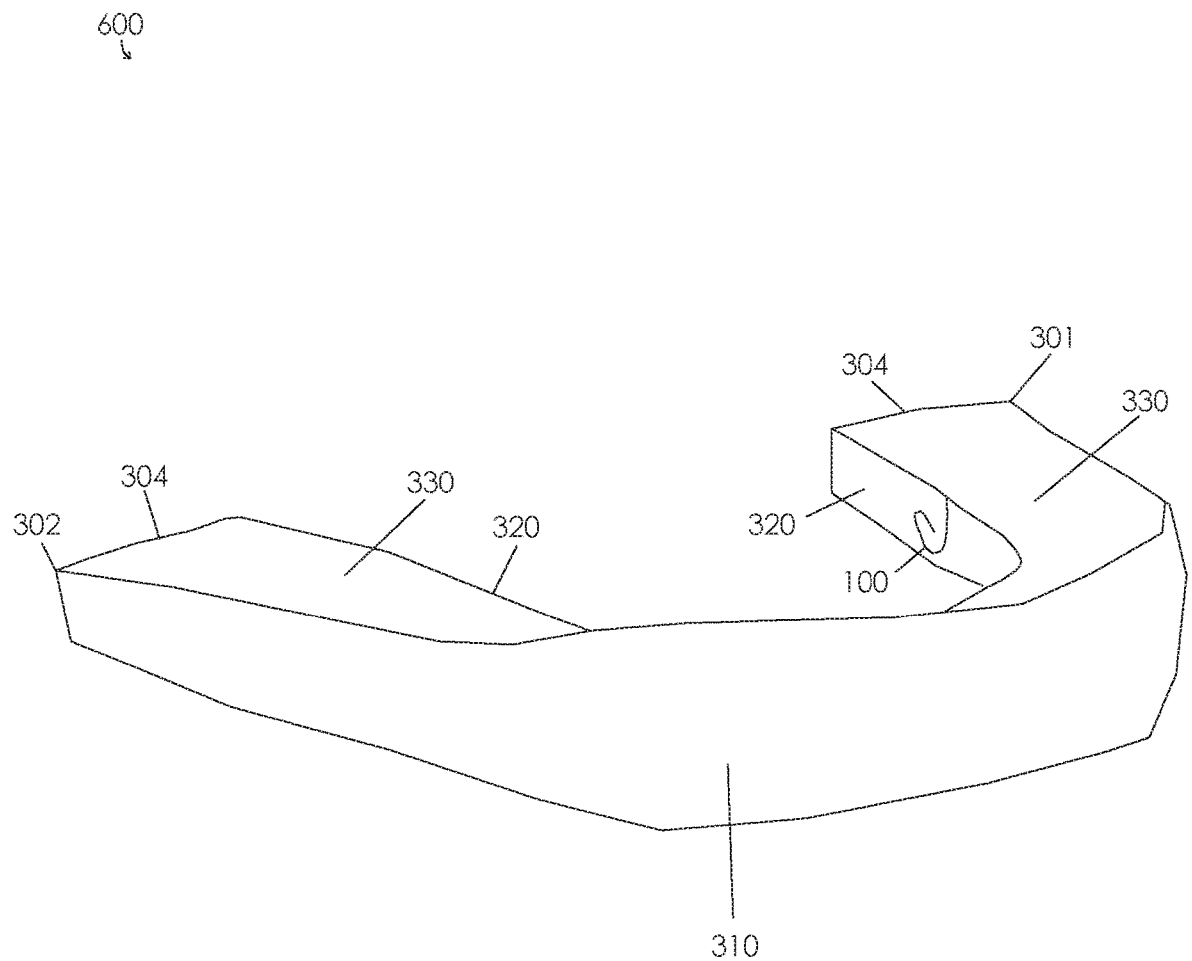
FIG. 6 is a schematic diagram illustrating an anchor system attached to an aligner for a maxillary dental arch.

FIG. 6 is a schematic diagram illustrating an anchor system attached to an aligner for a maxillary dental arch 600. Illustratively, anchor system 100 may be attached to any portion of aligner 300. In one or more embodiments, anchor system 100 may be attached to a portion of aligner distal end 301. Illustratively, anchor system 100 may be attached to a portion of aligner proximal end 302. In one or more embodiments, anchor system 100 may be attached to a portion of aligner superior end 303. Illustratively, anchor system 100 may be attached to a portion of aligner inferior end 304. In one or more embodiments, anchor system 100 may be attached to a portion of aligner lateral margin 310. Illustratively, anchor system 100 may be attached to a portion of aligner medial margin 320. In one or more embodiments, anchor system 100 may be attached to a portion of housing for teeth 330. Illustratively, anchor system 100 may be attached to any portion of aligner 300 without modifying aligner 300, e.g., anchor system 100 may be attached to any portion of aligner 300 without removing one or more portions of aligner 300. In one or more embodiments, anchor system 100 may be attached to any portion of aligner 300 wherein aligner 300 is manufactured by an additive manufacturing process and not modified before an attachment of anchor system 100. Illustratively, anchor system 100 may be attached to a modified portion of aligner 300, e.g., a practitioner may modify aligner 300 by removing portions of aligner 300 to create one or more slots in a portion of aligner 300 wherein a portion of anchor system 100 is disposed in at least one slot of the one or more slots. In one or more embodiments, a practitioner may modify aligner 300 by removing portions of aligner 300 to create a recessed portion along aligner lateral margin 310 wherein a portion of anchor system 100 is disposed in the recessed portion along aligner lateral margin 310. Illustratively, a practitioner may modify aligner 300 by removing portions of aligner 300 to create a recessed portion along aligner medial margin 320 wherein a portion of anchor system 100 is disposed in the recessed portion along aligner medial margin 320. In one or more embodiments, a practitioner may apply a force to a patient's tooth by attaching anchor system 100 to a portion of aligner 300 and disposing elastic band 200 in elastic band receptacle 109 wherein elastic band 200 is also disposed over a button bonded to the patient's tooth. Illustratively, a practitioner may apply a force to a patient's tooth by attaching anchor system 100 to a wire of the patient's dental braces and disposing elastic band 200 in elastic band receptacle 109 wherein elastic band 200 is also disposed over a bracket of the patient's dental braces. In one or more embodiments, anchor system 100 may be configured to reduce a number of aligners 300 required to treat a patient, e.g., anchor system 100 may eliminate the need for at least one aligner in a patient's aligner treatments.

Figure 7:
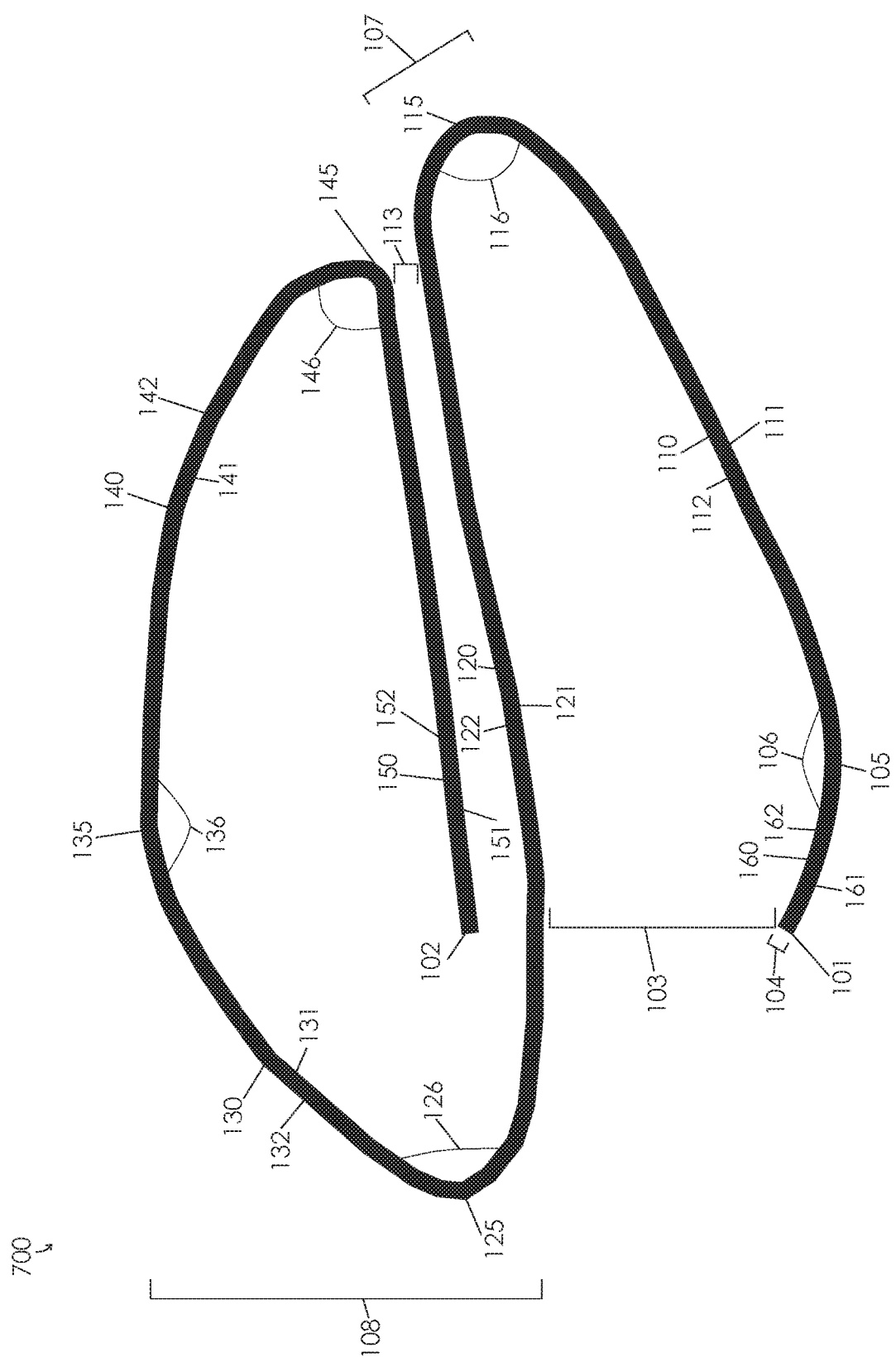
FIG. 7 is a schematic diagram illustrating an anchor system.

FIG. 7 is a schematic diagram illustrating an anchor system 700. In one or more embodiments, an anchor system 700 may comprise an anchor system distal end 101 and an anchor system proximal end 102. Illustratively, anchor system 700 may comprise an aligner receptacle 103 and an anchor mechanism 108. In one or more embodiments, aligner receptacle 103 may comprise an aligner housing 107, an aligner inferior interface limb 110, and an aligner superior interface limb 120. Illustratively, aligner superior interface limb 120 may comprise an aligner superior interface limb inferior surface 121 and an aligner superior interface limb superior surface 122. In one or more embodiments, aligner inferior interface limb 110 may comprise an aligner inferior interface limb inferior surface 111 and an aligner inferior interface limb superior surface 112. Illustratively, aligner housing 107 may be disposed between aligner inferior interface limb 110 and aligner superior interface limb 120, e.g., aligner housing 107 may be disposed between aligner inferior interface limb superior surface 112 and aligner superior interface limb inferior surface 121.

Illustratively, anchor system 700 may comprise a spring mechanism 160 having a spring mechanism inferior surface 161 and a spring mechanism superior surface 162. In one or more embodiments, spring mechanism 160 may have a spring mechanism thickness 104 configured to minimize patient discomfort. Illustratively, spring mechanism thickness 104 may comprise a length between spring mechanism inferior surface 161 and spring mechanism superior surface 162. In one or more embodiments, spring mechanism thickness 104 may be length in a range of 0.01 to 0.30 millimeters, e.g., spring mechanism thickness 104 may be a length of 0.10 millimeters. Illustratively, spring mechanism thickness 104 may be a length of less than 0.01 millimeters or greater than 0.30 millimeters.

In one or more embodiments, anchor system 700 may comprise a first joint 105 and a first joint angle 106. Illustratively, spring mechanism 160 may be disposed between anchor system distal end 101 and first joint 105. In one or more embodiments, first joint 105 may be configured to connect spring mechanism 160 and aligner inferior interface limb 110, e.g., first joint 105 may be disposed between spring mechanism 160 and aligner inferior interface limb 110. Illustratively, first joint angle 106 may comprise any angle greater than or equal to 90.0 degrees, e.g., first joint angle 106 may comprise an angle in a range of 90.0 to 180.0 degrees. In one or more embodiments, first joint angle 106 may comprise an angle in a range of 120.0 to 175.0 degrees, e.g., first joint angle 106 may comprise an angle of 165.0 degrees. Illustratively, first joint angle 106 may comprise an angle less than 120.0 degrees or greater than 175.0 degrees.

In one or more embodiments, anchor system 700 may comprise a second joint 115 and a second joint angle 116. Illustratively, aligner inferior interface limb 110 may be disposed between first joint 105 and second joint 115. In one or more embodiments, second joint 115 may be configured to connect aligner inferior interface limb 110 and aligner superior interface limb 120, e.g., second joint 115 may be disposed between aligner inferior interface limb 110 and aligner superior interface limb 120. Illustratively, second joint angle 116 may comprise any angle less than or equal to 90.0 degrees, e.g., second joint angle 116 may comprise an angle in a range of 10.0 to 90.0 degrees. In one or more embodiments, second joint angle 116 may comprise an angle in a range of 20.0 to 80.0 degrees, e.g., second joint angle 116 may comprise an angle of 65.0 degrees. Illustratively, second joint angle 116 may comprise an angle less than 20.0 degrees or greater than 80.0 degrees.

In one or more embodiments, anchor mechanism 108 may comprise an anchor mechanism anterior limb 130, an anchor mechanism posterior limb 140, and an elastic band retaining limb 150. Illustratively, anchor mechanism anterior limb 130 may comprise an anchor mechanism anterior limb inferior surface 131 and an anchor mechanism anterior limb superior surface 132. In one or more embodiments, anchor system 700 may comprise a third joint 125 and a third joint angle 126. Illustratively, third joint 125 may be configured to connect anchor mechanism anterior limb 130 and aligner superior interface limb 120, e.g., third joint 125 may be disposed between anchor mechanism anterior limb 130 and aligner superior interface limb 120. In one or more embodiments, third joint angle 126 may comprise any angle less than or equal to 100.0 degrees, e.g., third joint angle 126 may comprise an angle in a range of 20.0 to 100.0 degrees. Illustratively, third joint angle 126 may comprise an angle in a range of 30.0 to 90.0 degrees, e.g., third joint angle 126 may comprise an angle of 75.0 degrees. In one or more embodiments, third joint angle 126 may comprise an angle less than 30.0 degrees or greater than 90.0 degrees.

Illustratively, anchor mechanism posterior limb 140 may comprise an anchor mechanism posterior limb inferior surface 141 and an anchor mechanism posterior limb superior surface 142. In one or more embodiments, anchor system 700 may comprise a fourth joint 135 and a fourth joint angle 136. Illustratively, fourth joint 135 may be configured to connect anchor mechanism posterior limb 140 and anchor mechanism anterior limb 130, e.g., fourth joint 135 may be disposed between anchor mechanism posterior limb 140 and anchor mechanism anterior limb 130. In one or more embodiments, fourth joint angle 136 may comprise any angle greater than or equal to 90.0 degrees, e.g., fourth joint angle 136 may comprise an angle in a range of 90.0 to 180.0 degrees. Illustratively, fourth joint angle 136 may comprise an angle in a range of 110.0 to 175.0 degrees, e.g., fourth joint angle 136 may comprise an angle of 170.0 degrees. In one or more embodiments, fourth joint angle 136 may comprise an angle of less than 110.0 degrees or greater than 175.0 degrees.

Illustratively, elastic band retaining limb 150 may comprise an elastic band retaining limb inferior surface 151 and an elastic band retaining limb superior surface 152. In one or more embodiments, anchor system 700 may comprise a fifth joint 145 and a fifth joint angle 156. Illustratively, fifth joint 145 may be configured to connect elastic band retaining limb 150 and anchor mechanism posterior limb 140, e.g., fifth joint 145 may be disposed between elastic band retaining limb 150 and anchor mechanism posterior limb 140. In one or more embodiments, fifth joint angle 146 may comprise any angle less than or equal to 170.0 degrees, e.g., fifth joint angle 146 may comprise an angle in a range of 45.0 to 165.0 degrees. Illustratively, fifth joint angle 146 may comprise an angle in a range of 80.0 to 150.0 degrees, e.g., fifth joint angle 146 may comprise an angle of 125.0 degrees. In one or more embodiments, fifth joint angle 146 may comprise an angle of less than 80.0 degrees or greater than 150.0 degrees.

Illustratively, elastic band retaining limb 150 may be disposed between anchor system proximal end 102 and fifth joint 145. In one or more embodiments, elastic band retaining limb 150 may be disposed between anchor mechanism posterior limb 140 and aligner superior interface limb 120, e.g., elastic band retaining limb 150 may be disposed between anchor mechanism posterior limb inferior surface 141 and aligner superior interface limb superior surface 122. Illustratively, elastic band retaining limb 150 may be disposed between anchor mechanism anterior limb 130 and aligner superior interface limb 120, e.g., elastic band retaining limb 150 may be disposed between anchor mechanism anterior limb inferior surface 131 and aligner superior interface limb superior surface 122. In one or more embodiments, elastic band retaining limb 150 may be disposed between anchor mechanism posterior limb 140 and aligner inferior interface limb 110, e.g., elastic band retaining limb 150 may be disposed between anchor mechanism posterior limb inferior surface 141 and aligner inferior interface limb superior surface 112. Illustratively, elastic band retaining limb 150 may be disposed between anchor mechanism anterior limb 130 and aligner inferior interface limb 110, e.g., elastic band retaining limb 150 may be disposed between anchor mechanism anterior limb inferior surface 131 and aligner inferior interface limb superior surface 112.

In one or more embodiments, aligner superior interface limb 120 may be disposed between third joint 125 and second joint 115, e.g., third joint 125 may be configured to connect aligner superior interface limb 120 to anchor mechanism anterior limb 130 and second joint 115 may be configured to connect aligner superior interface limb 120 to aligner inferior interface limb 110. Illustratively, aligner superior interface limb 120 may be disposed between elastic band retaining limb 150 and aligner inferior interface limb 110, e.g., aligner superior interface limb 120 may be disposed between elastic band retaining limb inferior surface 151 and aligner inferior interface limb superior surface 112.

In one or more embodiments, aligner superior interface limb 120 may be disposed between anchor mechanism posterior limb 140 and aligner inferior interface limb 110, e.g., aligner superior interface limb 120 may be disposed between anchor mechanism posterior limb inferior surface 141 and aligner inferior interface limb superior surface 112. Illustratively, aligner superior interface limb 120 may be disposed between anchor mechanism anterior limb 130 and aligner inferior interface limb 110, e.g., aligner superior interface limb 120 may be disposed between anchor mechanism anterior limb inferior surface 131 and aligner inferior interface limb superior surface 112. In one or more embodiments, aligner superior interface limb 120 may be disposed between elastic band retaining limb 150 and spring mechanism 160, e.g., aligner superior interface limb 120 may be disposed between elastic band retaining limb inferior surface 151 and spring mechanism superior surface 162. Illustratively, aligner superior interface limb 120 may be disposed between anchor mechanism posterior limb 140 and spring mechanism 160, e.g., aligner superior interface limb 120 may be disposed between anchor mechanism posterior limb inferior surface 141 and spring mechanism superior surface 162.

In one or more embodiments, anchor system 700 may comprise a first elastic band ingress aperture 113. Illustratively, first elastic band ingress aperture 113 may be disposed between elastic band retaining limb 150 and aligner superior interface limb 120, e.g., first elastic band ingress aperture 113 may be disposed between elastic band retaining limb inferior surface 151 and aligner superior interface limb superior surface 122. In one or more embodiments, first elastic band ingress aperture 113 may be the only elastic band ingress aperture of anchor system 700, e.g., anchor system 700 may comprise a single elastic band ingress aperture.

Illustratively, anchor system 700 may be manufactured from any suitable material, e.g., polymers, metals, metal alloys, etc., or from any combination of suitable materials. In one or more embodiments, anchor system 700 may be manufactured from spring steel, e.g., anchor system 700 may be manufactured from a shape memory material. In one or more embodiments, anchor system 700 may be manufactured from stainless steel, e.g., anchor system 700 may be manufactured from Type 301 stainless steel, Type 302 stainless steel, Type 303 stainless steel, Type 304 stainless steel, Type 304L stainless steel, Type 304LN stainless steel, Type 310 stainless steel, Type 316 stainless steel, Type 316L stainless steel, Type 316Ti stainless steel, Type 321 stainless steel, Type 430 stainless steel, Type 440 stainless steel, Type 17-7 stainless steel, etc. Illustratively, anchor system 700 may be manufactured from nitinol. In one or more embodiments, anchor system 700 may be manufactured from aluminum, e.g., anchor system 700 may be manufactured from an aluminum alloy. Illustratively, anchor system 700 may be manufactured from a 6061 aluminum alloy, a 6061-T4 aluminum alloy, a 6061-T6 aluminum alloy, a 6063 aluminum alloy, a 6063 aluminum alloy, etc. In one or more embodiments, anchor system 700 may be manufactured from titanium, e.g., anchor system 700 may be manufactured from a titanium alloy. Illustratively, anchor system 700 may be manufactured from a Grade 5 titanium alloy, a Grade 6 titanium alloy, a Grade 7 titanium alloy, a Grade 7H titanium alloy, a Grade 9 titanium alloy, a Grade 11 titanium alloy, a Grade 12 titanium alloy, a Grade 16 titanium alloy, a Grade 17 titanium alloy, a Grade 18 titanium alloy, etc.

In one or more embodiments, a portion of anchor system 700 that may contact a patient's tooth may be manufactured from a material having a hardness of less than 4.2 GPa to prevent the portion of anchor system 700 from damaging the patient's tooth enamel. Illustratively, a portion of anchor system 700 that may contact a patient's tooth may be coated with a material having a hardness of less than 4.2 GPa to prevent the portion of anchor system 700 from damaging the patient's tooth enamel. In one or more embodiments, a portion of anchor system 700 may be manufactured from a material having a hardness in a range of 1.2 to 3.6 GPa to prevent damage to a patient's tooth enamel, e.g., a portion of anchor system 700 may be manufactured from a material having a hardness of 3.5 GPa to prevent damage to a patient's tooth enamel. Illustratively, a portion of anchor system 700 may be covered by a sleeve having a hardness of less than 4.2 GPa configured to prevent damage to a patient's tooth enamel, e.g., aligner inferior interface limb 110 may be covered by a sleeve having a hardness of less than 4.2 GPa. In one or more embodiments, spring mechanism 160 may be covered by a sleeve having a hardness of less than 4.2 GPa configured to prevent damage to a patient's tooth enamel. Illustratively, a portion of anchor system 700 may be wrapped in a cordage having a hardness of less than 4.2 GPa, e.g., a portion of anchor system 700 may be wrapped in a cordage configured to prevent damage to a patient's tooth enamel. In one or more embodiments, a portion of anchor system 700 may be coated by an epoxy having a hardness of less than 4.2 GPa when cured, e.g., a portion of anchor system 700 may be coated by an epoxy configured to prevent damage to a patient's tooth enamel when cured. Illustratively, a portion of anchor system 700 may be electropolished to prevent damage to a patient's tooth enamel.

Figure 8:
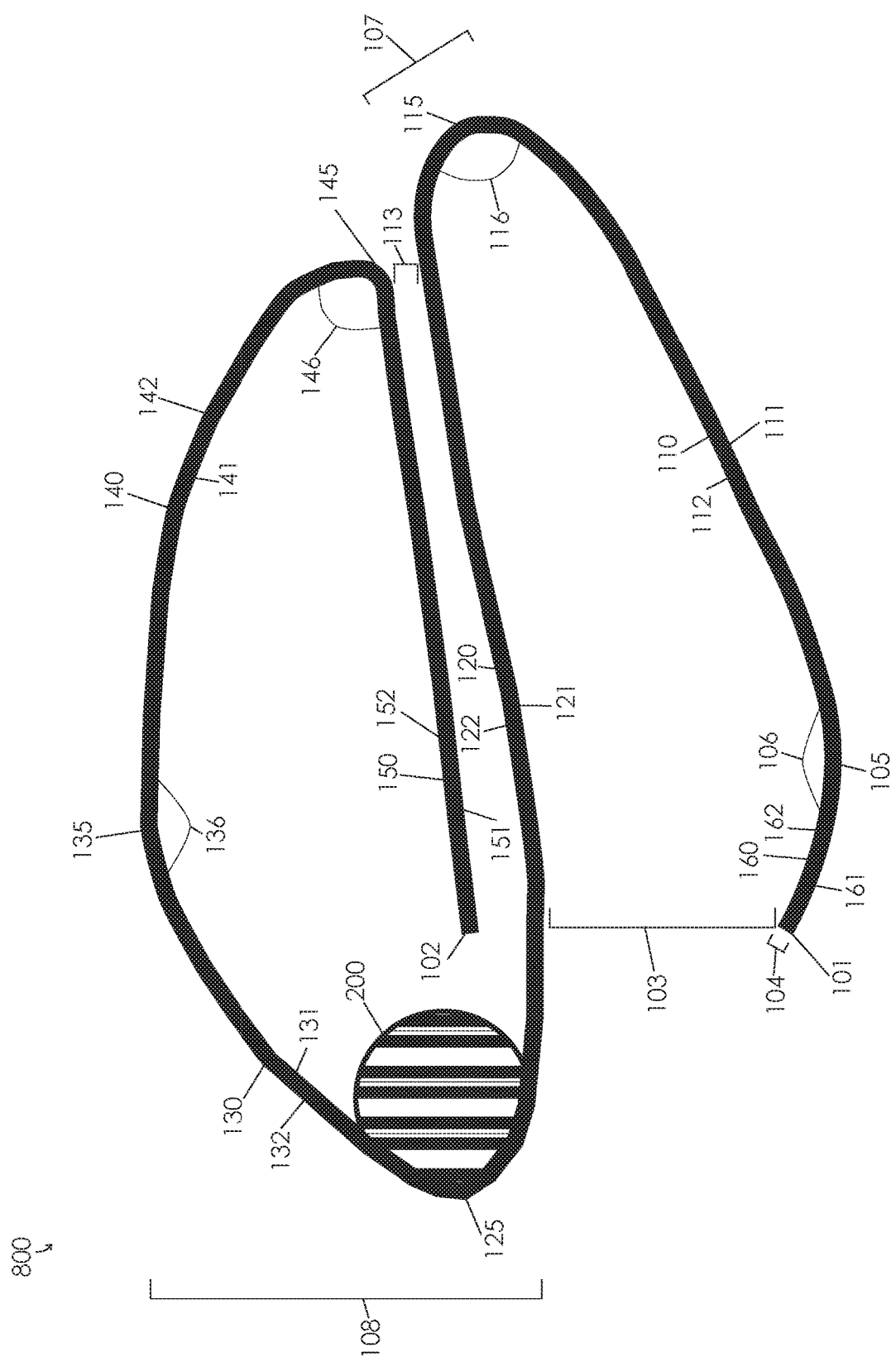
FIG. 8 is a schematic diagram illustrating an elastic band attached to an anchor system.

FIG. 8 is a schematic diagram illustrating an elastic band attached to an anchor system 800. In one or more embodiments, a portion of elastic band 200 may be adjacent to a portion of third joint 125 when elastic band 200 and anchor system 700 comprise an elastic band attached to an anchor system 800, e.g., a portion of elastic band 200 may abut a portion of third joint 125 when elastic band 200 and anchor system 700 comprise an elastic band attached to an anchor system 800. Illustratively, a portion of elastic band 200 may be adjacent to a portion of anchor mechanism anterior limb 130 when elastic band 200 and anchor system 700 comprise an elastic band attached to an anchor system 800, e.g., a portion of elastic band 200 may abut a portion of anchor mechanism anterior limb inferior surface 131 when elastic band 200 and anchor system 700 comprise an elastic band attached to an anchor system 800. In one or more embodiments, a portion of elastic band 200 may be adjacent to a portion of aligner superior interface limb 120 when elastic band 200 and anchor system 700 comprise an elastic band attached to an anchor system 800, e.g., a portion of elastic band 200 may abut a portion of aligner superior interface limb superior surface 122 when elastic band 200 and anchor system 700 comprise an elastic band attached to an anchor system 800. Illustratively, elastic band 200 may be disposed between aligner superior interface limb 120 and anchor mechanism anterior limb 130 when elastic band 200 and anchor system 700 comprise an elastic band attached to an anchor system 800, e.g., elastic band 200 may be disposed between aligner superior interface limb superior surface 122 and anchor mechanism anterior limb inferior surface 131 when elastic band 200 and anchor system 700 comprise an elastic band attached to an anchor system 800. In one or more embodiments, elastic band 200 may be disposed between third joint 125 and elastic band retaining limb 150 when elastic band 200 and anchor system 700 comprise an elastic band attached to an anchor system 800, e.g., elastic band 200 may be disposed between third joint 125 and anchor system proximal end 102 when elastic band 200 and anchor system 700 comprise an elastic band attached to an anchor system 800. Illustratively, elastic band 200 may be disposed in anchor mechanism 108 when elastic band 200 and anchor system 700 comprise an elastic band attached to an anchor system 800.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of an orthodontic anchor system, the teachings of the present invention are equally suitable to any systems where the functionality may be employed. Therefore, it is the object of the appended claims to cover all such variations and modifications as come within the true spirit and scope of the invention.

What is claimed is:

1. A system including an orthodontic anchor and an aligner, the system comprising:

a spring mechanism having a spring mechanism inferior surface and a spring mechanism superior surface wherein the spring mechanism has a thickness in a range of 0.01 to 0.30 millimeters, the spring mechanism configured to apply a force to a portion of the aligner;

an aligner inferior interface limb having an aligner inferior interface limb inferior surface and an aligner inferior interface limb superior surface;

a first joint disposed directly between the spring mechanism and the aligner inferior interface limb, the first joint directly connecting the spring mechanism and the aligner inferior interface limb;

an aligner superior interface limb having an aligner superior interface limb inferior surface and an aligner superior interface limb superior surface;

an aligner housing wherein the aligner housing is disposed between the aligner inferior interface limb and the aligner superior interface limb;

a second joint disposed directly between the aligner superior interface limb and the aligner inferior interface limb, the second joint directly connecting the aligner superior interface limb and the aligner inferior interface limb;

an anchor mechanism anterior limb having an anchor mechanism anterior limb inferior surface and an anchor mechanism anterior limb superior surface;

a third joint disposed directly between the anchor mechanism anterior limb and the aligner superior interface limb, the third joint directly connecting the anchor mechanism anterior limb and the aligner superior interface limb wherein the aligner superior interface limb is disposed directly between the third joint and the second joint;

an elastic band retaining limb having an elastic band retaining limb inferior surface and an elastic band retaining limb superior surface wherein the elastic band retaining limb is disposed between the anchor mechanism anterior limb and the aligner inferior interface limb;

an elastic band ingress aperture wherein the elastic band ingress aperture is disposed between the elastic band retaining limb and the aligner superior interface limb; and an anchor mechanism posterior limb having an anchor mechanism posterior limb inferior surface and an anchor mechanism posterior limb superior surface wherein the elastic band retaining limb is disposed between the anchor mechanism posterior limb and the aligner superior interface limb.

2. The system of claim 1 further comprising:
a first joint angle of the first joint in a range of 90.0 to 180.0 degrees.

3. The system of claim 2 further comprising:
a second joint angle of the second joint in a range of 10.0 to 90.0 degrees.

4. The system of claim 3 further comprising:
a third joint angle of the third joint in a range of 20.0 to 100.0 degrees.

5. The system of claim 1 further comprising:
a fourth joint disposed between the anchor mechanism anterior limb and the anchor mechanism posterior limb, the fourth joint connecting the anchor mechanism anterior limb and the anchor mechanism posterior limb.

6. The system of claim 5 further comprising:
a fifth joint disposed between the anchor mechanism posterior limb and the elastic band retaining limb, the fifth joint connecting the anchor mechanism posterior limb and the elastic band retaining limb.

7. The system of claim 6 further comprising:
a fourth joint angle in a range of 90.0 to 180.0 degrees.

8. The system of claim 7 further comprising:
a fifth joint angle in a range of 11.0 to 71.0 degrees.

9. The system of claim 1 wherein the system is manufactured from spring steel.

10. The system of claim 1 wherein the system is manufactured from stainless steel.

11. The system of claim 1 wherein the system is manufactured from a shape memory material.

12. The system of claim 11 wherein the system is manufactured from nitinol.

13. The system of claim 1 wherein the system is manufactured from titanium.

14. The system of claim 1 wherein the system is manufactured from aluminum.

15. The system of claim 1 wherein the spring mechanism has a thickness of 0.10 millimeters.

16. The system of claim 1 wherein an elastic band is disposed between the anchor mechanism posterior limb inferior surface and the elastic band retaining limb superior surface.

17. The system of claim 1 wherein a portion of the aligner is disposed between the aligner superior interface limb inferior surface and the aligner inferior interface limb superior surface.

18. The system of claim 17 wherein the portion of the aligner is housed in the aligner housing.

19. A system including an orthodontic anchor and an aligner, the system comprising:
a spring mechanism having a spring mechanism inferior surface and a spring mechanism superior surface, the spring mechanism having a coating configured to prevent damage to a patient's tooth enamel;
an aligner inferior interface limb having an aligner inferior interface limb inferior surface and an aligner inferior interface limb superior surface;
a first joint disposed between the spring mechanism and the aligner inferior interface limb, the first joint connecting the spring mechanism and the aligner inferior interface limb;
an aligner superior interface limb having an aligner superior interface limb inferior surface and an aligner superior interface limb superior surface;
an aligner housing wherein the aligner housing is disposed between the aligner inferior interface limb and the aligner superior interface limb, the aligner housing configured to house the aligner;
a second joint disposed between the aligner superior interface limb and the aligner inferior interface limb, the second joint connecting the aligner superior interface limb and the aligner inferior interface limb;
an anchor mechanism anterior limb having an anchor mechanism anterior limb inferior surface and an anchor mechanism anterior limb superior surface;
a third joint disposed directly between the anchor mechanism anterior limb and the aligner superior interface limb, the third joint directly connecting the anchor mechanism anterior limb and the aligner superior interface limb wherein the aligner superior interface limb is disposed directly between the third joint and the second joint;
an elastic band retaining limb having an elastic band retaining limb inferior surface and an elastic band retaining limb superior surface wherein the elastic band retaining limb is disposed between the anchor mechanism anterior limb and the aligner inferior interface limb;
an elastic band ingress aperture wherein the elastic band ingress aperture is disposed between the elastic band retaining limb and the aligner superior interface limb; and
an anchor mechanism posterior limb having an anchor mechanism posterior limb inferior surface and an anchor mechanism posterior limb superior surface wherein the elastic band retaining limb is disposed between the anchor mechanism posterior limb and the aligner superior interface limb.

20. A system including an orthodontic anchor and an aligner, the system comprising:
a spring mechanism having a spring mechanism inferior surface and a spring mechanism superior surface, the spring mechanism covered by a sleeve;
an aligner inferior interface limb having an aligner inferior interface limb inferior surface and an aligner inferior interface limb superior surface;
a first joint disposed between the spring mechanism and the aligner inferior interface limb, the first joint connecting the spring mechanism and the aligner inferior interface limb;
an aligner superior interface limb having an aligner superior interface limb inferior surface and an aligner superior interface limb superior surface;
an aligner housing wherein the aligner housing is disposed between the aligner inferior interface limb and the aligner superior interface limb, the aligner housing configured to house the aligner;
a second joint disposed between the aligner superior interface limb and the aligner inferior interface limb, the second joint connecting the aligner superior interface limb and the aligner inferior interface limb;
an anchor mechanism anterior limb having an anchor mechanism anterior limb inferior surface and an anchor mechanism anterior limb superior surface;
a third joint disposed directly between the anchor mechanism anterior limb and the aligner superior interface limb, the third joint directly connecting the anchor mechanism anterior limb and the aligner superior interface limb wherein the aligner superior interface limb is disposed directly between the third joint and the second joint;

an elastic band retaining limb having an elastic band retaining limb inferior surface and an elastic band retaining limb superior surface wherein the elastic band retaining limb is disposed between the anchor mechanism anterior limb and the aligner inferior interface limb;

an elastic band ingress aperture wherein the elastic band ingress aperture is disposed between the elastic band retaining limb and the aligner superior interface limb; and an anchor mechanism posterior limb having an anchor mechanism posterior limb inferior surface and an anchor mechanism posterior limb superior surface wherein the elastic band retaining limb is disposed between the anchor mechanism posterior limb and the aligner superior interface limb.

* * * * *